United States Patent [19]
Gelfand et al.

[11] Patent Number: 5,504,093
[45] Date of Patent: Apr. 2, 1996

[54] METHOD FOR INHIBITING NUCLEOSIDE AND NUCLEOBASE TRANSPORT IN MAMMALIAN CELLS, AND METHOD FOR INHIBITION OF DNA VIRUS REPLICATION

[75] Inventors: Erwin W. Gelfand; Naohiro Terada, both of Englewood, Colo.

[73] Assignee: Otsuka Pharmaceutical Co., Ltd., Tokyo, Japan

[21] Appl. No.: 283,707

[22] Filed: Aug. 1, 1994

[51] Int. Cl.$^6$ .................................................. A61K 31/47
[52] U.S. Cl. ........................................................ 514/314
[58] Field of Search ............................................ 514/314

[56] References Cited

U.S. PATENT DOCUMENTS 4,415,572  11/1983  Tominaga et al. ...................... 424/250

FOREIGN PATENT DOCUMENTS

| 552373A1 | 7/1993 | European Pat. Off. . |
|---|---|---|
| 6192097 | 7/1994 | Japan . |
| 6192096 | 7/1994 | Japan . |
| 6192095 | 7/1994 | Japan . |
| 6192094 | 7/1994 | Japan . |
| 9311769 | 6/1993 | WIPO . |
| 9420107 | 9/1994 | WIPO . |

OTHER PUBLICATIONS

Sasayama et al, "Acute Hemodynamic Effects of a New Inotropic Agent, OPC–8212, On Severe Congestive Heart Failure", *Heart and Vessels*, 2(1):23–28 (1986).

Lueprasitsukul et al, "Effect of the Cardiac Inotropic Drug, OPC 8212, on Pituitary–Thyroid Function in the Rat, " *Endocrinology*, 128(6):2709–2714 (1991).

Berkow, Editor–in–Chief, "The Merck Manual of Diagnosis and Therapy", 15th Edition, Merck Sharp & Dohme Research Laboratories, Rahway, N.J., pp. 1043–1050 (1987).

Bush et al, "Effect of OPC–8212, A New Positive Intropic Agent, on the Hemopoietic System In Vitro", *Experimental Hematology*, 19(6):490 (1991).

Nakai et al, "Differentiation–Inducing Activity of 3,4–dihydro–6–[4–(3,4–dimethoxybenzoyl)–1–piperazinyl]–2(1H)–quinolinone (vesnarinone) Against Tumor Leukemia and Solid Tumor Cells, " *Biomedicine & Pharmacotherapy*, 46(5–7):308 (1992).

Miller, "Epstein–Barr Virus: Biology, Pathogenesis, and Medical Aspects", *Virology*, 2nd Edition, Chapter 68, pp. 1921–1958 (1990).

Matsumori et al, "Vesnarinone, a New Inotropic Agent, Inhibits Cytokine Production by Stimulated Human Blood From Patients With Heart Failure", *Circulation*, 89(3):955–958 (1994).

Shioi et al, "Inhibition of Cytokine Production by a New Inotropic Agent, Vesnarinone, In Human Lymphocytes, T Cell Line, and Monocytic Cell line", *Life Sciences*, 54:11–16 (1994).

Meyerhans et al, "Restriction and Enhancement of Human Immunodeficiency Virus Type 1 Replication by Modulation of Intracellular Deoxynucleoside Triphosphate Pools", *J. Virol.*, 68(1):535–540 (1994).

O'Brien et al, "Kinetics of Human Immunodeficiency Virus Type 1 Reverse Transcription in Blood Mononuclear Phagocytes are Slowed by Limitations of Nucleotide Precursors", *J. Virol.*, 68(2):1258–1263 (1994).

Gao et al, "Low levels of Deoxynucleotides in Peripheral Blood Lymphocytes: A Strategy to Inhibit Human Immunodeficiency Virus Type 1 Replication", *Proc. Natl. Acad. Sci. USA* 90:8925–8928 (1993).

Maruyama et al, "Vesnarinone Inhibits Production of HIV–1 in Cultured Cells", *Biochemical and Biophysical Research Communications*, 195(3):1264–1271 (1993).

Datta et al, "Acyclovir Inhibition of Epstein–Barr Virus Replication", *Proc. Natl. Acad. Sci. USA* 77(9):5163–5166 (1980).

*Primary Examiner*—José G. Dees
*Assistant Examiner*—Deborah D. Carr
*Attorney, Agent, or Firm*—Sughrue, Mion, Zinn, Macpeak & Seas

[57] ABSTRACT

A method for inhibiting nucleoside and nucleobase transport in mammalian cells, as well as to a method for inhibition of DNA virus replication are disclosed, wherein each method uses, as the active agent, a carbostyril derivative.

2 Claims, 14 Drawing Sheets

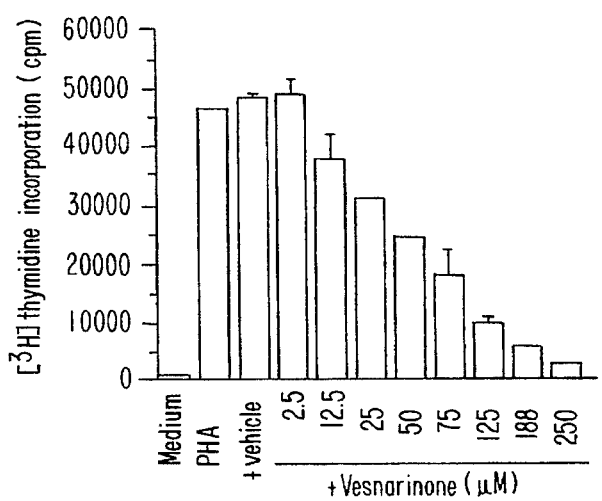
FIG. 1A
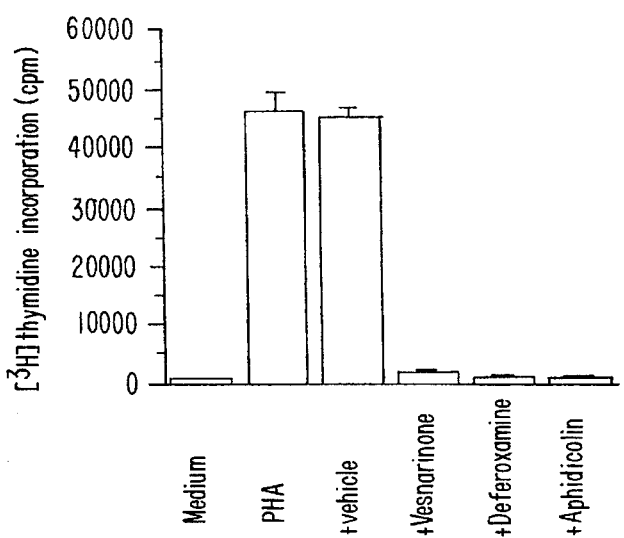
FIG. 1B
FIG. 1C
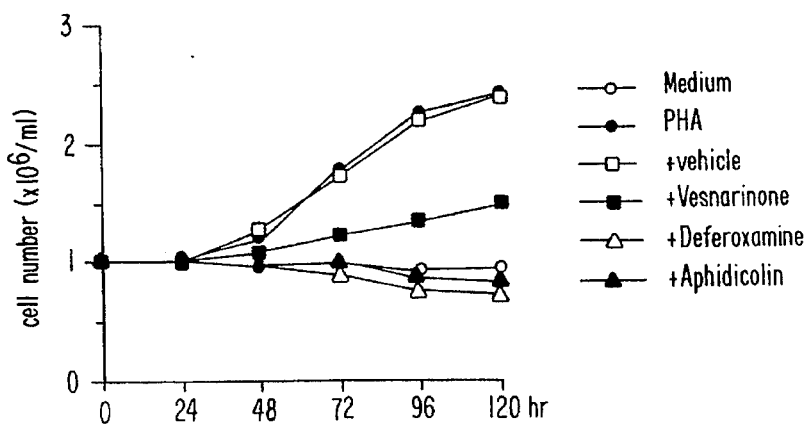

Raji cells

—○— adenosine
—●— adenine

Raji cells

—○— adenosine
—●— adenine

CHO cells

—○— adenosine
—●— adenine

← ZEBRA

Vesnarinone   −   −   +   −   +
            ―――   ―――――   ―――――
            0hr    3hr      20hr

FIG. 8B ← R(BRLF1)

Vesnarinone   −   −   +   −   +
            ―――   ―――――   ―――――
            0hr    3hr      20hr

← EA-R(BHRF1)

Vesnarinone   −   +   −   +
            ―――――   ―――――
             3hr      20hr

∃ EA-D(BMRF1)

Vesnarinone   −   +   −   +
            ―――――   ―――――
             3hr      20hr

METHOD FOR INHIBITING NUCLEOSIDE AND NUCLEOBASE TRANSPORT IN MAMMALIAN CELLS, AND METHOD FOR INHIBITION OF DNA VIRUS REPLICATION

FIELD OF THE INVENTION

The present invention relates to a method for inhibiting nucleoside and nucleobase transport in mammalian cells, as well as to a method for inhibition of DNA virus replication, wherein each method uses, as the active agent, a carbostyril derivative.

BACKGROUND OF THE INVENTION

I. Carbostyrils

Carbostyril derivatives represented by the following general formula (1), and salts thereof:

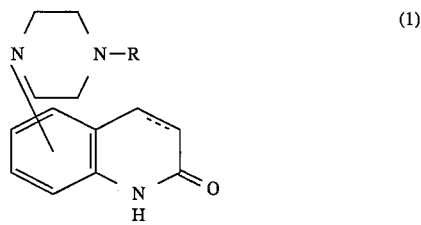

wherein R is a benzoyl group which may optionally have lower alkoxy groups on the phenyl ring as substituents and the carbon-carbon bond in the 3 and 4 positions of the carbostyril skeleton is a single bond or double bond, are well-known in the art (U.S. Pat. No. 4,415,572, which is incorporated by reference herein in its entirety).

These carbostyrils have been found to be useful as an oral inotropic agent for treatment of patients with congestive heart failure (U.S. Pat. No. 4,415,572; and Hori et al, *Jpn. Circ. J.*, 50:659–666 (1986)). Several studies have demonstrated that the above carbostyrils improve hemodynamic indexes, and exercise capacity in congestive heart failure patients (Inoue et al, *Heart Vessels*, 2:166–171 (1986); Sasayama et al, *Heart Vessels*, 2:23–28 (1986); and Feldman et al, *Am. Heart J.*, 116:771–777 (1988)). In addition, multi-center randomized placebo-controlled trials both in Japan and in the United States demonstrated that these carbostyrils improve both quality of life and reduced the risk of death in patients with congestive heart failure (OPC-8212 Multicenter Research Group, *Cardiovasc. Drugs Ther.*, 4:419–425 (1990); Feldman et al, *Am. J. Cardiol.*, 68:1203–1210 (1991); and Feldman et al, *N. Engl. J. Med.*, 329:149–155 (1993)).

The mechanisms of action associated with the inotropic properties of these carbostyrils include a decrease in potassium current (Iijima et al, *J. Pharmacol. Exp. Ther.*, 240:657–662 (1987)), a mild inhibition of phosphodiesterase, and an increase in the inward calcium current (Yatani et al, *J. Cardiovasc. Pharmacol.*, 13:812–819 (1989); and Taira et al, *Arzneimittelforschung*, 4:347–355 (1984)). However, the dose of the carbostyrils which was most effective in reducing mortality (60 mg daily) showed no or little hemodynamic effect, implying that the drug may reduce mortality through another mechanism, rather than its positive inotropic effect (Feldman et al, . *N. Engl. J. Med.*, 329:149–155 (1993); and Packer, *N. Engl. J. Med.*, 329:201–202 (1993)).

The above carbostyrils are also known to inhibit the production of various cytokines, including TNF-α and IL-6, by lipopolysaccharide-stimulated peripheral blood mononuclear cells (PBMC) in a dose-dependent manner (Maruyama et al, *Biochem. Biophys. Res. Commu.*, 195:1264–1271 (1993); and Matsumori et al, *Circul.*, 89:955–958 (1994)).

Moreover, they can induce a reversible neutropenia associated with a decrease in CFU-C (Feldman et al, *Am. Heart J.*, 11 :771–777 (1988); OPC-8212 Multicenter Research Group, *Cardiovasc. Drugs, Ther.*, 4:419–425 (1990); Feldman et al, *Am. J. Cardiol.*, 68:1203–1210 (1991); and Feldman et al, *N. Endl J. Med.*, 329.:149–155 (1993)).

Additionally, the above carbostyrils have been found to be useful in regulating apoptosis (programmed cell death), and in the treatment of cancer, inhibition of tumor metastasis and inhibition of RNA virus replication (U.S. patent application Ser. No. 07/989,028, filed Apr. 30, 1993, which corresponds to European Patent Publication 0552373, each of which is incorporated by reference herein in their entirety; Nakai et al, *Jpn. J. Cancer Res.*, Abstract, and *Proc. Jpn. Cancer Assoc.*, page 581 (1993); and Maruyama et al, *Biochem. Biophys Res.* Comm., 195:1264–1271 (1993)).

It has been surprising to find in the present invention that these carbostyrils, particularly the species 3,4-dihydro-6-[4-(3,4-dimethoxybenzoyl)- 1-piperazinyl]-2(1H)-quinoline (hereinafter "vesnarinone"), inhibit nucleoside and nucleobase transport in mammalian cells, as the structures of these compounds are entirely different from the structure of known compounds which inhibit nucleoside and nucleobase transport.

II. Epstein-Barr Virus

Epstein-Barr virus (EBV), a human lymphotropic herpes group DNA ,virus, infects human B lymphocytes, and is linked to a variety of lymphoproliferative diseases (Miller et al, *Virol.*, Second Edition, pages 1921–1958 (1990)). There are several reports indicating that the reactivation of EBV may be linked to the development of B-cell mediated autoimmunity (Fox, *J. Virol. Methods*, 21:19–27 (1988); Fox et al, *Springer Semin. Immunopathol.*, 13:217–231 (1991); and Logtenberg et al, *Immunol. Rev.*, 128:23–47 (1992)).

EBV persists in B lymphocytes as a latent infection in vivo and in vitro. In its latent form, the EBV genome exists in a circular episomal form, and gene expression is relatively limited (Sample et al, *J. Virol.*, 64:1667–1974 (1990)). In vitro, the expression of latent genes is associated with immortalization and with resistance of host cells to apoptosis, related, at least in part, to the up-regulation of bcl-2 gene expression (Henderson et al, *Cell*, 65:1107–1115 (1991); and Gregory et al, *Nature*, 349:612–614 (1991)). Replication of the EBV genome in the latent phase is controlled by host cell polymerases, and occurs strictly during S-phase of the host cell cycle (Adams, *J. Virol.*, 61:1743–1746 (1987)).

Various reagents including phorbol esters, n-butyrate, halogenated pyrimidines, calcium ionophores, and anti-immunoglobulin (Ig) antibodies can initiate the switch into the lytic or productive EBV replication phase in latently infected B lymphocytes (Tovey et al, *Nature*, 276:270–272 (1978); Gerber, *Proc. Natl. Acad. USA*, 69:83–85 (1972); Faggioni et al, *Science*, 232:1554–1556 (1986); Takada, *Int. J. Cancer*, 3:27–32 (1984); and Takagi et al, *Virol.*, 185:309–315 (1991)). Replication of EBV genome in the productive phase, where a large number of infectious EBV virions are produced, is independent of host cell DNA replication, but can be affected by alteration of the intracellular deoxynucleobase pool (Datta et al, *Proc. Natl. Acad. Sci. USA*, 77:5163–5166 (1980)). Clinicopathologically, entry into the productive phase, of the EBV cycle is purported to play an important role in the reactivation of EBV infection in vivo.

It has been surprising to find in the present invention that the above carbostyrils, particularly vesnarinone, are useful in inhibiting DNA virus replication, as evidenced by the data in an EBV model system.

SUMMARY OF THE INVENTION

An object of the present invention is to provide a method for inhibiting nucleoside and nucleobase transport in a mammalian cell.

Another object of the present invention is to provide a method for inhibiting DNA virus replication.

A further object of the present invention is to provide a method for treatment of EBV infection.

These and other objects of the present invention, which will be apparent from the detailed description of the invention provided hereinafter, have been met by the use of a carbostyril derivative represented by the following general formula (1), and salts thereof:

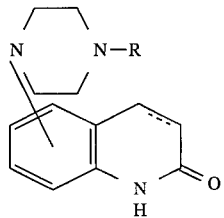

(1)

wherein R is a benzoyl group which may optionally have lower alkoxy groups on the phenyl ring as substituents and the carbon-carbon bond in the 3 and 4 positions of the carbostyril skeleton is a single bond or double bond.

BRIEF DESCRIPTION OF THE DRAWINGS

FIGS. 1A–1B show [$^3$H]thymidine incorporation by human T cells stimulated for 48 hrs with 10 µg/ml PHA in the presence of 0–250 µM vesnarinone (FIG. 1A); and in the presence of RPMI 1640 medium, in the absence of any drug, in the presence of HEPES buffer, and in the presence of 250 µM vesnarinone, 100 µM deferoxamine or 15 nM aphidicolin (FIG. 1B). FIG. 1C shows cell numbers after human T cells are stimulated for 0–120 hrs with 10 µg/ml PHA (●) in the presence of RPMI 1640 medium in the absence of any drug (o), in the presence of HEPES buffer (□), 250 µM vesnarinone (■), 100 µM deferoxamine (Δ) or 15 nM aphidicolin (▲).

FIGS. 8A–8D represent Western blots of lysates from DMSO-released Akata cells stimulated with 50 µg/ml of anti-IgG antibody in the absence (−) or presence of vesnarinone at a concentration of 30 µg/ml (+). The products of BZLF1 (ZEBRA) (FIG. 8A); BRLF1 (R) (FIG. 8B); BHRF1 (EA-R) (FIG. 8C); and BMRF1 (EA-D) (FIG. 8D) were assayed by Western blotting of lysates from the cells harvested 3 hrs and 20 hrs after stimulation with anti-IgG.

FIGS. 12A–2C represent Western blots of lysates from four different Burkitt's lymphoma cell lines, i.e., Akata, P3HR1, Jijoye, and Raji, cultured in the absence (−) or presence (+) of 20 µg/ml vesnarinone for 7 days. Two EBV latent gene products, EBNA2 (FIG. 12A) and LMP1 (FIG. 12B), and one host gene product, bcl-2 (FIG. 12C), were evaluated.

Figure 13A:
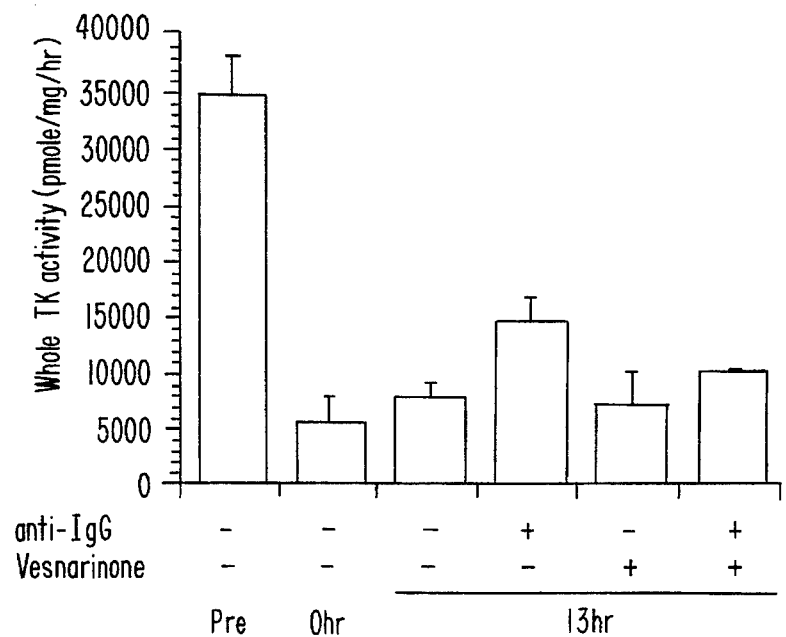
FIGS. 13A–13B show thymidine kinase assays of extracts from DMSO-released Akata cell stimulated without (−) or with (+) 50 µg/ml of anti-IgG antibody in the presence (+)
Figure 13B:
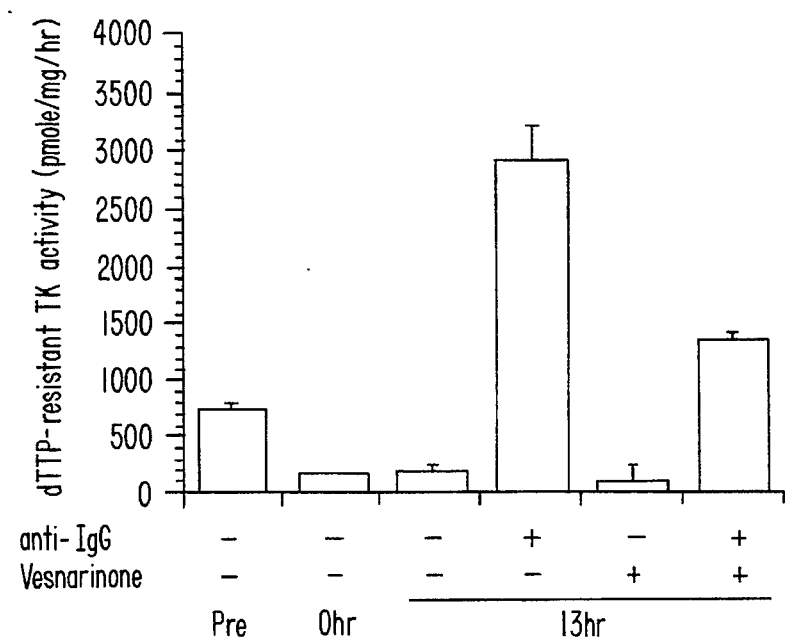

or absence (−) of 100 μg/ml vesnarinone for 13 hrs. Whole thymidine kinase activity was measured in the absence of dTTP (FIG. 13A). For determining dTTP-resistant thymidine kinase activity, 100 μM dTTP was added to the kinase reaction mixture (FIG. 13B).

DETAILED DESCRIPTION OF THE INVENTION

In general formula (1), the benzoyl group which may have lower alkoxy groups and substituents on the phenyl ring, includes benzoyl groups having 1 to 3 straight-chain or branched $C_{1-6}$ alkoxy groups substituting the phenyl ring, such as benzoyl, 2-methoxybenzoyl, 3-methoxybenzoyl, 4-methoxybenzoyl, 2-ethoxybenzoyl, 3-ethoxybenzoyl, 4-ethoxybenzoyl, 4-isobutoxybenzoyl, 4-hexloxybenzoyl, 3,4-dimethoxybenzoyl, 3,4-diethoxybenzoyl, 3,4,5-trimethoxybenzoyl, 2,5-dimethoxybenzoyl, and soon.

Of the active ingredient compound (1) according to the invention, 6-[4-(3,4-dimethoxybenzoyl)- 1-piperazinyl]-3, 4-dihydrocarbostyril, i.e.,vesnarinone is most preferable.

The above carbostyrils will readily form a salt with a conventional acid. As such acids, there may be mentioned inorganic acids, such as sulfuric acid, nitric acid, hydrochloric acid and hydrobromic acid; and organic acids, such as acetic acid, p-toluenesulfonic acid, ethanesulfonic acid, oxalic acid, maleic acid, fumaric acid, citric acid, succinic acid and benzoic acid. These salts can also be used as the active ingredient in the present invention, just as can the free compound of general formula (1).

The compounds of general formula (1) and salts thereof, can be generally formulated into the per se conventional pharmaceutical preparations. Such preparations are prepared using conventional fillers, extenders, binding agents, moistening agents, disintegrating agents, surfactants, lubricants, and the like diluents or excipient. These pharmaceutical preparations may have various dosage forms selected according to the purposes of therapy, and typical examples thereof are tablets, pills, powders, solutions, suspensions, emulsions, granules, capsules, suppositories, injections (solutions, suspensions, etc.), and ophthalmic solutions.

For the manufacture of tablets, a wide variety of carriers so far well-known in this field can be used. Thus, use can be made of, for example, vehicles or excipient, such as lactose, sucrose, sodium chloride, glucose, urea, starch, calcium carbonate, kaolin, crystalline cellulose and silicic acid; binding agents, such as water, ethanol, propanol, simple syrup, glucose solution, starch solution, gelatin solution, carboxymethylcellulose, shellac, methylcellulose, potassium phosphate and polyvinylpyrrolidone; disintegrating agents, such as dry starch, sodium alginate, powdered agar, powdered laminaran, sodium hydrogen carbonate, calcium carbonate, polyoxyethylene sorbitan fatty acid esters, sodium lauryl sulfate, stearic acid monoglyceride, starch and lactose; disintegration inhibitors, such as sucrose, stearin, cacao butter and hydrogenated oils; absorption promoters, such as quaternary ammonium bases and sodium lauryl sulfate; wetting agents or humectants, such as glycerol and starch; adsorbents, such as starch, lactose, kaolin, bentonite and colloidal silica; and lubricants, such as refined talc, stearic acid salts, powdered boric acid and polyethylene glycol. When necessary, the tablets may further be provided with a conventional coating to give, for example, sugar-coated tablets, gelatin-coated tablets, enteric-coated tablets, film-coated tablets, or double-coated or multilayer tablets.

For the manufacture of pills, a wide variety of carriers well-known in the art can be used. Examples are vehicles or excipients, such as glucose, lactose, starch, cacao butter, hardened vegetable oils, kaolin and talc; binding agents, such as powdered gum arabic, powdered tragacanth gum, gelatin and ethanol; and disintegrating agents, such as laminaran and agar.

For the manufacture of suppositories, a wide variety of known carriers can be used. As examples, there may be mentioned polyethylene glycol, cacao butter, higher alcohols, higher alcohol esters, gelatin and semisynthetic glycerides.

In preparing injections, the solutions or suspensions are preferably sterilized and are preferably isotonic with blood and, for preparing such dosage forms, all of the diluents in conventional use in the field can be employed. Thus, for example, water, ethyl alcohol, propylene glycol, ethoxylated isostearyl alcohol, polyoxylated isostearyl alcohol and polyoxyethylene sorbitan fatty acid esters may be mentioned. In this case, the pharmaceutical preparations may contain sodium chloride, glucose or glycerol in an amount sufficient to give isotonic solutions. It is possible to add conventional solubilizing agents, buffers, soothing agents or local anesthetics, etc.

Furthermore, when necessary, the pharmaceutical preparations may contain coloring matters, preservatives, perfumes, flavoring agents, sweetening agents and the like, as well as other drugs.

The proportion of the active ingredient compound in these pharmaceutical preparations for use in the present invention is not critical, and may suitably be selected over a wide range. Generally, however, the proportion is recommendably selected within the range of about 1.0 to about 70% by weight, preferably about 1.0 to about 30% by weight.

The route of administration of the pharmaceutical preparations of the present invention is not critical, either, but is selected according to the dosage form, the patient's age, sex and other factors, and the severity of the disease to be treated. Thus, for instance, when they are provided in the form of tablets, pills, solutions, suspensions, emulsions, granules or capsules, the preparations are administered orally. Injectable solutions are administered intravenously, either alone or in admixture with conventional fluids for parental infusion containing glucose, amino acids and so on. Where necessary, these solutions may also be administered as is by the intramuscular, intradermal, subcutaneous or intraperitoneal route. Suppositories are administered rectally, ophthalmic solutions are drop lotions for the eyes.

While the dosage of the above pharmaceutical preparations is dependent on the method of administration, the patient's age, sex and other background factors, severity of the disease and so on, it is generally recommended to administer about 0.5 to 30 mg, as the active ingredient, viz. compound (1), per kilogram body weight per day. The amount of the active ingredient to be contained in each dosage unit is about 10 to 1000 mg.

| Dosage Form Example 1 | |
|---|---|
| 6-[4-(3,4-Dimethoxybenzoyl)-1-piperazinyl]-3,4-dihydrocarbostyril | 150 g |
| Avicel | 40 g |
| (trademark, Asahi Chemical Industry, Co., Ltd.) | |
| Corn starch | 30 g |
| Magnesium stearate | 2 g |
| Hydroxypropylmethylcellulose | 10 g |
| Polyethylene glycol 6000 | 3 g |
| Castor oil | 40 g |
| Methanol | 40 g |

The above active ingredient, Avicel, corn starch and magnesium stearate are mixed and ground together, and the resulting mixture is compression-molded with a dragee R10 mm punch. The tablets thus obtained are coated with a film coating composition consisting of hydroxypropyl methylcellulose, polyethylene glycol 6000, castor oil and methanol to give

| Dosage Form Example 2 | |
| --- | --- |
| 6-[4-(3,4-Dimethoxybenzoyl-1-piperazinyl]-3,4-dihydrocarbostyril | 150.0 g |
| Citric acid | 1.0 g |
| Lactose | 33.5 g |
| Dicalcium phosphate | 70.0 g |
| Pluronic F-68 | 30.0 g |
| Sodium lauryl sulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium lauryl sulfate | 3.0 g |
| Dry magnesium stearate | 3.0 g |
| Ethanol | q.s. |

The above active ingredient, citric acid, lactose, dicalcium phosphate, pluronic F-68 and sodium lauryl sulfate are admixed.

After size selection using a No. 60 screen, the mixture is granulated by the wet process using an alcoholic solution containing polyvinylpyrrolidone, Carbowax 1500 and Carbowax 6000. When necessary, alcohol is added to make the powder into a paste-like mass. Then, corn starch is added, and the blending is continued until uniform granules are formed. The mixture is then passed through a No. 10 screen, placed in a tray and dried in an oven maintained at 100° C. for 12 to 14 hrs. The dried granules are sieved through a No. 16 screen, then dry sodium lauryl sulfate and dry magnesium stearate are added and, after blending, the mixture is compressed to a desired size and shape using a tableting machine.

The above cores are treated with a varnish and dusted with talc for preventing absorption of moisture, and then provided with an undercoat layer. Varnish coating is repeated as many times as sufficient for internal use. The tablets are rendered completely round and smooth by application of a further undercoat layer and a smooth coating. Color coating is conducted until a desired coloring is obtained. After drying, the coated tablets are polished to give uniformly polished tablets.

The DNA viruses whose replication can be inhibited in the present invention include: herpes simplex virus type 1 and 2, human herpes virus type 6, herpes zoster virus, human cytomegalovirus and EBV. EBV is the preferred DNA virus whose replication can be inhibited in the present invention.

Thus, the above carbostyrils are useful in the treatment of disorders associated with chronic EBV infection, e.g., chronic fatigue syndrome and chronic infectious mononucleosis; EBV-associated lymphoma, e.g., Burkitt's lymphoma, B Cell lymphoma, T cell lymphoma, nasopharyngeal carcinoma and Hodgkin's disease; or EBV-induced lymphoproliferative; or EBV-associated autoimmune disease, e.g., Sjögren syndrome.

In addition, in the methods of inhibiting DNA virus replication, and particularly treating EBV infection, the carbostyrils of the present invention can be used in combination with other known anti-DNA virus compounds, particularly, other known commercially available anti-EBV compounds, such as Acyclovir (9-[(2-hydroxyethoxy)methyl]guanine) (Burroughs Wellcome); and Ganciclovir sodium (9-[[2-hydroxy-1-(hydroxymethyl)ethoxy]methyl]guanine) (Syntex). In this manner, the dosage conventionally used for the known anti-DNA virus compounds can be reduced.

The following examples are provided for illustrative purposes only, and are in no way intended to limit the scope of the present invention.

EXAMPLE 1

A. Vesnarinone Blocks Nucleoside Incorporation Immediately After Addition of the Drug Vesnarinone has been reported to have a mild cytostatic effect depending on the cell type tested (Nakai et al, *Jpn. J. Cancer Res.*, Abstract, *Proc. Jpn. Cancer Assoc.*, page 581 (1993)). Thus, in order to investigate the mechanism of action of vesnarinone, nucleoside or nucleobase transport into cells was measured as described by Aronow et al, *J. Biol. Chem.*, 260:16274–16278 (1985).

More specifically, human primary T cells were separated from peripheral blood obtained by leukopheresis of healthy donors. Mononuclear cell suspensions were prepared by Ficoll-Hypaque gradient centrifugation, and T cells were obtained by E-rosette enrichment as described by Kumagai et al, *J. Cell. Physiol.*, 137:329 (1988). The resulting T cells were stimulated for 48 hrs with 10 µg/ml phytohemagglutinin (PHA), in the absence of any drug (referred to as "PHA") and in the presence of HEPES buffer (referred to as "vehicle") as controls, or in the presence of 0–250 µM vesnarinone, prepared as described below.

10 mg of vesnarinone was dissolved in 0.5 ml of 2.0 N HCl. The solution was added to 9.0 ml of RPMI 1640 medium supplemented with 20 mM HEPES buffer (pH 7.55), and neutralized to pH 7.0 by addition of 2.0 N NaOH. The resulting neutralized vesnarinone solution containing 1.0 mg/ml of vesnarinone was immediately filtered using a 0.45 µm Millipore filter, and added to the cell cultures (1 µg/ml≈2.5 µM of vesnarinone).

Next, the cells were resuspended in RPMI 1640 medium (GIBCO, Grand Island, NY) supplemented with 10% (v/v) heat-inactivated fetal bovine serum (FBS, HyClone, Logan, UT), 2.0 mM L-glutamine (GIBCO), 100 U/ml penicillin and 100 µg/ml streptomycin (GIBCO), and containing 20 mM HEPES (pH 7.4), and incubated for 20 min at 37° C.

Then, 1.0 µCi of [$^3$H]thymidine (6.7 Ci/mmole, ICN), was added to 2.0×10$^6$ cells (100 µl), and the cells were pulse-labeled for 6 hrs. Next, the mixture was immediately layered on silicone oil/paraffin oil (94:6) in microfuge tubes, and the cells were separated from free [$^3$H]substrate in the water phase by spinning for 1 min at 14,000 rpm.

The water and oil phases were discarded, and the radioactivity in the cell pellets was measured using liquid scintillation counting. The results are shown in FIG. 1A.

As shown in FIG. 1A, vesnarinone inhibits [$^3$H]thymidine incorporation into DNA in a dose-dependent manner.

Next, 15 µM aphidicolin and 100 µM deferoxamine were obtained, and utilized as described by Terada et al, *J. Immuno*, 147:698–704 (1991). The results are shown in FIG. 1B.

As shown in Figure 1B, addition of aphidicolin, which inhibits DNA polymerase α/δ, or deferoxamine, which inhibits ribonucleobase reductase, also inhibited [$^3$H]thymidine incorporation.

Next, the effects of the above-described drugs on cell proliferation were evaluated over a period of 120 hrs. More specifically, the above experiment was repeated using 250 µM vesnarinone, 15 nM aphidicolin or 100 µM deferoxamine, and 10 µg/ml PHA. The results are shown in FIG. 1C.

As shown in FIG. 1C, a high dose of vesnarinone (250 µM) inhibited cell proliferation when compared to control cultures, but increases in cell number were nonetheless observed. In contrast, as shown in FIG. 1C, no increases in cell number were observed in the presence of aphidicolin or deferoxamine. Again all three drugs inhibited [$^3$H]thymidine incorporation to a similar degree at the doses indicated in FIG. 1B.

Next, cellular DNA content was evaluated over the 0–120 hrs treatment period. More specifically, $10^6$ T cells treated in the same manner as described above, were fixed with 70% (v/v) ethanol at 4° C. overnight, centrifuged and washed with phosphate buffered saline (PBS). The fixed cells were incubated with 0.5 ml of 0.25 mg/ml ribonuclease (Sigma, St. Louis, Mo.) in PBS at 37° C. for 10 min. The cell suspension was mixed with 0.5 ml of a 50 µg/ml propidium iodide (Calbiochem, La Jolla, Calif.) solution in PBS, and after 60 min analyzed by flow cytometry (EPICS Profile, Coulter, Hialeah, FL), collecting red fluorescence (>600 nm) with 488 nm excitation. The results are shown in FIGS. 2A–2F.

As shown in FIGS. 2A–2F, consistent with the increases in cell number, monitoring of cellular DNA content revealed that a certain proportion of the cells entered both S and G2/M phases of the cell cycle in the presence of vesnarinone within 48 hrs, but not in the presence of aphidicolin or deferoxamine. [$^3$H]thymidine incorporation was inhibited by vesnarinone to a similar degree at all time points throughout the experiment (up to 120 hrs), and there was no recovery of [$^3$H]thymidine incorporation at later time points. Thus, these results indicate that vesnarinone may inhibit [$^3$H]thymidine incorporation by a mechanism other than inhibition of DNA synthesis per se.

In order to further evaluate the interaction of vesnarinone on [$^3$H]thymidine and [$^3$H]uridine incorporation, the effects of brief exposure of proliferating cells to vesnarinone were examined.

More specifically, $10^6$ T cells were stimulated with 10 µg/ml PHA for 48 hrs in the presence of 250 µM vesnarinone or 15 nM aphidicolin or 100 µM deferoxamine, and [$^3$H] thymidine or [$^3$H]uridine (35.1 Ci/mmole, ICN) were added for only 30 min, and cell pellets were obtained and evaluated as described above. The results are shown in FIG. 3.

Figure 2A:
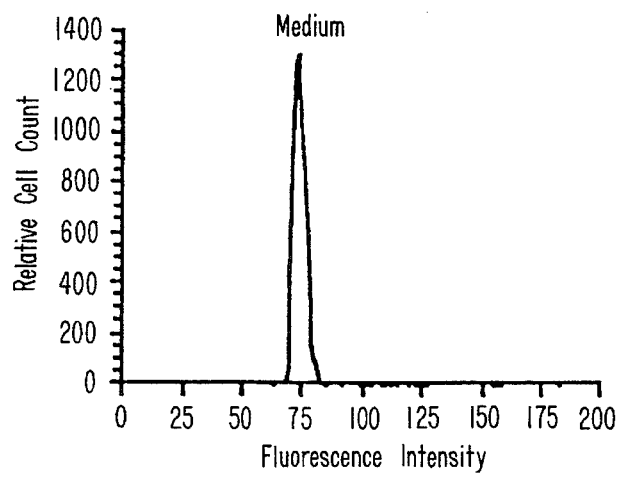
FIGS. 2A–2F show cellular DNA content, as measured by fluorescence intensity, determined after human T cells were stimulated for 0–120 hrs with: RPMI 1640 medium (FIG. 2A); 10 µg/ml PHA (FIG. 2B); 10 µg/ml PHA in the presence of HEPES buffer (FIG. 2C); 10 µg/ml PHA in the presence of 250 µM vesnarinone (FIG. 2D); 10 µg/ml PHA in the presence of 15 nM aphidicolin (FIG. 2D); or 10 µg/ml PHA in the presence of 100 µM deferoxamine (FIG. 2F).
Figure 2B:
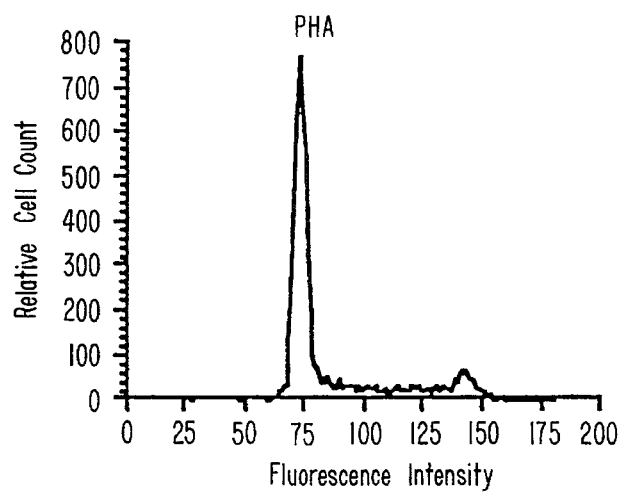
Figure 2C:
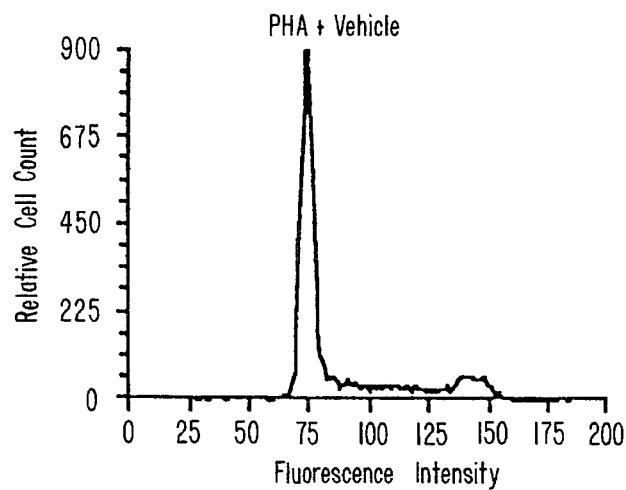
Figure 2D:
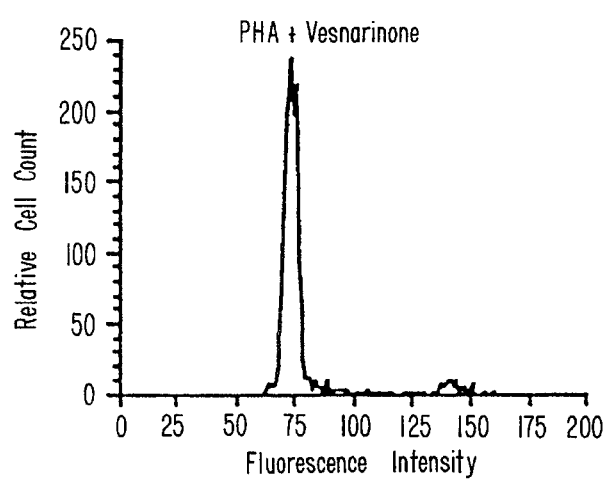
Figure 2E:
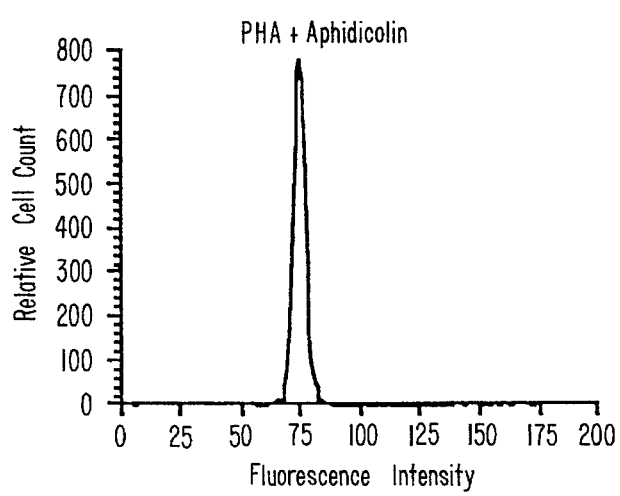
Figure 2F:
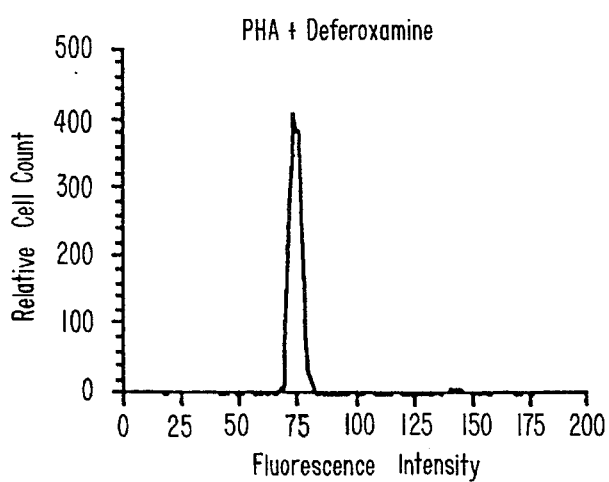
Figure 3:
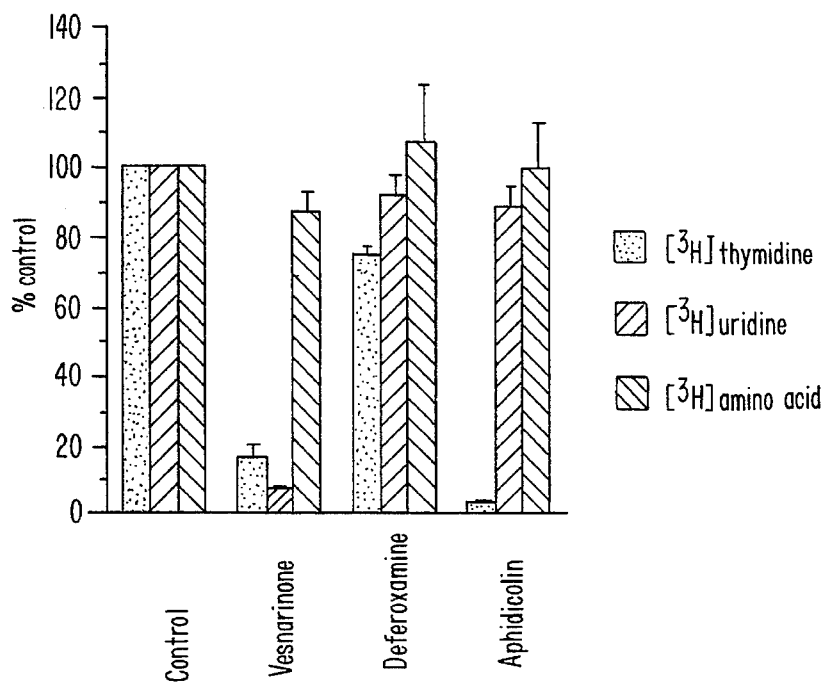
FIG. 3 shows [$^3$H]thymidine, [$^3$H]uridine and [$^3$H]amino acid incorporation by human T cells stimulated for 48 hrs with 10 µg/ml PHA in the presence of 250 µM vesnarinone, 100 µM deferoxamine 15 nM aphidicolin.

As shown in FIG. 3, vesnarinone and aphidicolin were able to inhibit [$^3$H]thymidine incorporation under these conditions as well. In contrast, as shown in FIG. 3, deferoxamine only partially inhibited [$^3$H]thymidine incorporation, likely because increases in dNTP pools in proliferating cells were sufficient to sustain DNA synthesis for a period of time without further supply of dNTP.

In addition, as shown in FIG. 3, vesnarinone rapidly inhibited [$^3$H]uridine incorporation as well. This was also in contrast to the very small effect on cellular RNA content, measured by flow cytometry following acridine orange staining of cells. Aphidicolin or deferoxamine did not inhibit [$^3$H]uridine incorporation.

Next, the PHA-stimulated T cells were labelled for 30 min with 5.0 µCi/ml of an [$^3$H]amino acid mixture (1.0 mCi/ml, Amersham, Arlington Heights, Ill.), washed twice with ice-cold PBS, and then lysed in PBS containing 1.0% (w/v) SDS, followed by addition of a mixture of 7.0% (w/v) trichloroacetic acid and 1.0% (w/v) pyrophosphate. The precipitates were loaded on GF/A filters, and washed extensively with a mixture of 7.0% (w/v) trichloroacetic acid and 1.0% (w/v) pyrophosphate. Radioactivity was measured by scintillation counting. The results are also shown in FIG. 3.

As shown in FIG. 3, vesnarinone did not inhibit [$^3$H] amino acid incorporation.

Thus, the profound and rapid inhibition of both [$^3$H] thymidine and [$^3$H]uridine incorporation by vesnarinone is not likely explained by a direct effect on DNA and RNA synthesis. The discrepancy suggests that vesnarinone may interfere with nucleoside incorporation into cells.

B. Vesnarinone Inhibits Nucleoside and Nucleobase Transport

Nucleosides permeate the plasma membrane of cells, and are utilized as a source for the salvage pathway of nucleobase synthesis (Cory, In: Biochemistry with Clinical Correlations, Chapter 13, pages 529–571 (1992); and Rodwell, In: Biochemistry, Chapter 36, pages 363–377 (1993)). The transport of nucleosides into mammalian cells occurs by a facilitated diffusion mechanism which appears to be mediated by a single or multiple carriers of variable specificity (Aronow et al, J. Biol. Chem., 261:14467–14473 (1986)). This carrier model is based on kinetic evidence indicating competitive inhibition among nucleosides for transport and on the results in mutant cells which are genetically deficient in nucleoside transport capability (Aronow et al, J. Biol. Chem., 261:14467–14473 (1986); Cohen et al, J. Biol. Chem., 254:112–116 (1979); and Ullman et al, Mol. Cell. Biol., 3:1187–1196 (1983)).

The study of nucleoside transport in mammalian cells has been greatly enhanced by the existence of specific high affinity inhibitors of the nucleoside transporter in mammalian cells, including 4-nitrobenzyl-6-thioinosine (NBMPR), dipyridamole and dilazep (Aronow et al, J. Biol. Chem., 260:6226–6233 (1985); Scholtissek et al, Biochem. Biophy . Acta, 158:435–447 (1968); Plagemann et al, J. Membr. Biol., 81:255–262 (1984); Berlin et al, Int. Rev. Cytol., 42:287–336 (1975); and Fujita et al, Br. J. Pharmacol., 68:343–349 (1980)). The entry of nucleobases, another physiological source for salvage nucleobase synthesis, is less well defined.

Nucleosides and nucleobases mutually interfere with the translocation of each other in some animal cells, suggesting a role for the nucleoside transporter in nucleobase transport (Aronow et al, J. Biol. Chem., 261:2014–2019 (1986)). On the other hand, the presence of independent nucleobase transport is suggested through studies using mutant cell lines (Aronow et al, J. Biol. Chem., 261:2014–2019 (1986)). Thus, the possibility that vesnarinone inhibits nucleoside transport was evaluated, by looking at rapid transport of radiolabelled nucleosides and nucleobases into T cells.

More specifically, $10^6$ T cells stimulated for 48 hrs with 10 µg/ml PHA were treated with 250 µM vesnarinone, 100 µM deferoxamine, 15 nM aphidicolin or 1.0 µM dipyridamole, and pulse-labelled for 1 min with [$^3$H]thymidine, [$^3$H]adenosine (23 Ci/mmole, Amersham) , [$^3$H]adenine (26 Ci/mmole, Amersham) or [$^3$H]uracil (53 Ci/mmole, Amersham), and cell pellets were obtained and evaluated as described above. The results are shown in FIG. 4.

Figure 4:
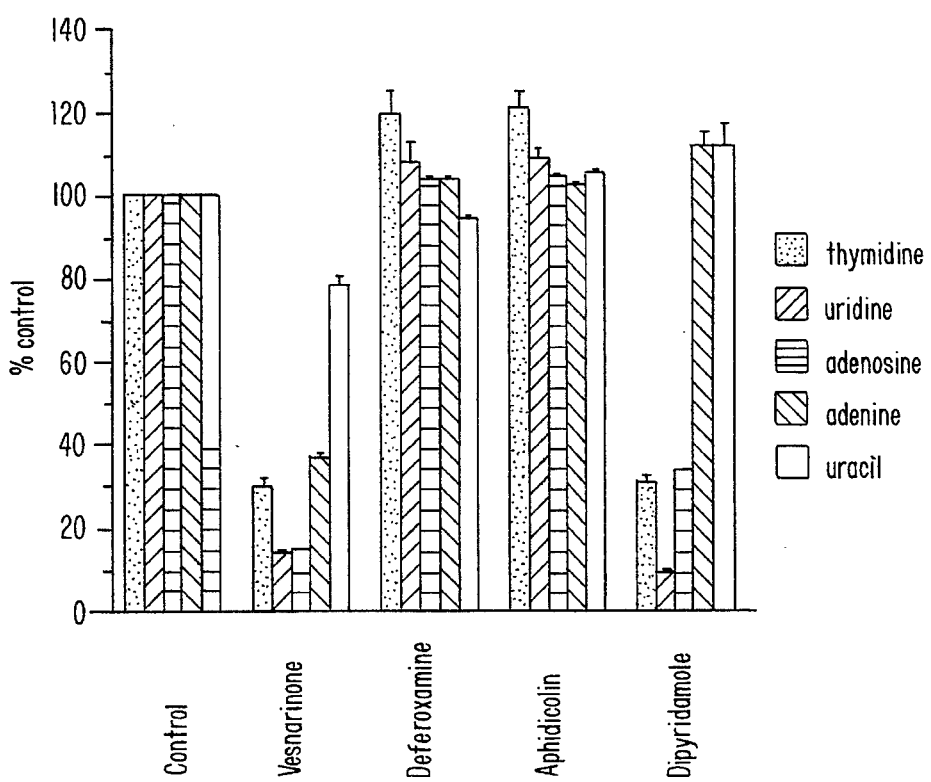
FIG. 4 shows the effects on [$^3$H]nucleoside or [$^3$H] nucleobase transport in human T cells stimulated for 48 hrs with 10 µg/ml PHA in the presence of 250 µM vesnarinone, 100 µM deferoxamine, 15 nM aphidicolin or 1.0 µM dipyridamole.

As shown in FIG. 4, vesnarinone inhibited transportation of [$^3$H]thymidine, [$^3$H]adenosine, [$^3$H]adenine, and also to a lesser extent, [$^3$H]uracil. In contrast, deferoxamine or aphidicolin had no effect on the transport of these nucleosides or nucleobases, despite using the same concentration of these drugs which inhibited [$^3$H]thymidine incorporation into DNA. In addition, dipyridamole, a specific high affinity inhibitor of a nucleoside transporter (Scholtissek et al, *Biochem. Biophys. Acta*, 158:435–447 (1968); and Plagemann et al, *J. Membr. Biol.*, 81:255–262 (1984)), suppressed nucleoside transport, but not nucleobase transport.

Next, dose-dependent responses to vesnarinone on nucleoside and nucleobase transport were examined using several different cell lines, i.e., human lymphoblastoid line, Raji, which was obtained from the American Type Culture Collection (ATCC No. CCL-86), and the Chinese hamster ovary cell line, CHO, which was provided by Dr. G.L. Johnson (Denver, Colo.).

More specifically, $2.0 \times 10^6$ Raji or CHO cells were treated with 0–750 μM vesnarinone or 0–100 μM dipyridamole, and pulse-labelled for 1 min with [$^3$H]adenine or [$^3$H]adenosine, and the cell pellets obtained and evaluated as described above. The results are shown in FIGS. 5A–5D.

Figure 5A:
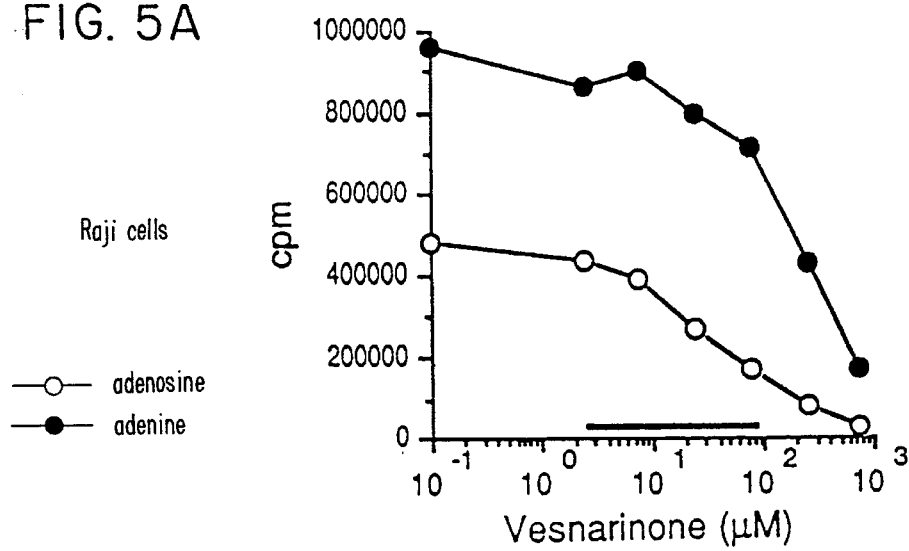
FIGS. 5A–5D show the dose-dependent effects of 0–750 µM vesnarinone on the transport of [$^3$H]adenosine (o) or [$^3$H]adenine (●) in Raji cells (FIG. 5A) or CHO cells (FIG. 5C); and the dose-dependent effects of 0–100 µM dipyridamole on the transport of [$^3$H]adenosine (o) or [$^3$H] adenine (●) in Raji cells (FIG. 5B) or CHO cells (FIG. 5D).
Figure 5B:
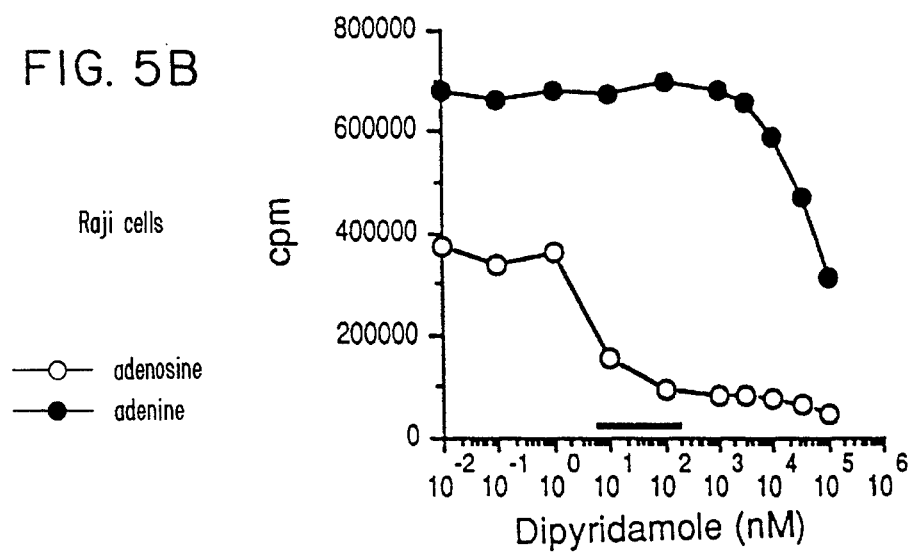
Figure 5C:
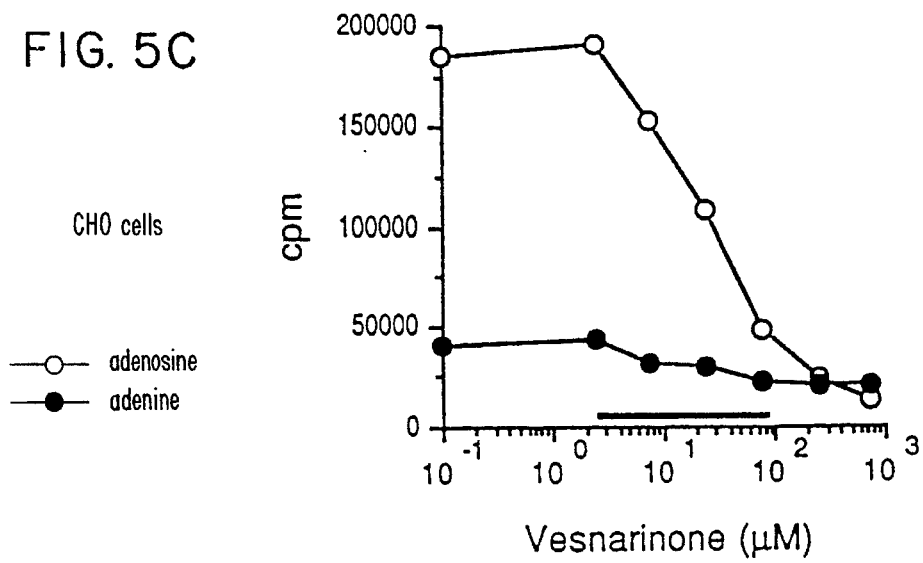

As shown in FIG. 5A, in the presence of vesnarinone, Raji cells had an increased ability to transport the purine nucleobase, [$^3$H]adenine in a dose-dependent manner, while, as shown in FIG. 5C, CHO cells, in the presence of vesnarinone, had a lesser ability to transport this nucleobase. In contrast, as shown in FIGS. 5A and 5C, in the presence of vesnarinone both cells showed a similar ability to transport the purine nucleoside, adenosine in a dose-dependent manner. Such variability is not surprising since variability, especially for nucleobase transport, has been reported previously (Aronow et al, *Mol. Cell Biol.*, 6:2957–2962 (1986)).

It should be noted that the inhibitory effects on nucleoside and nucleobase transport in vitro were observed within the therapeutic range of vesnarinone in vivo (2–80 μM) (shown as a bar in FIGS. 5A and 5C).

Figure 5D:
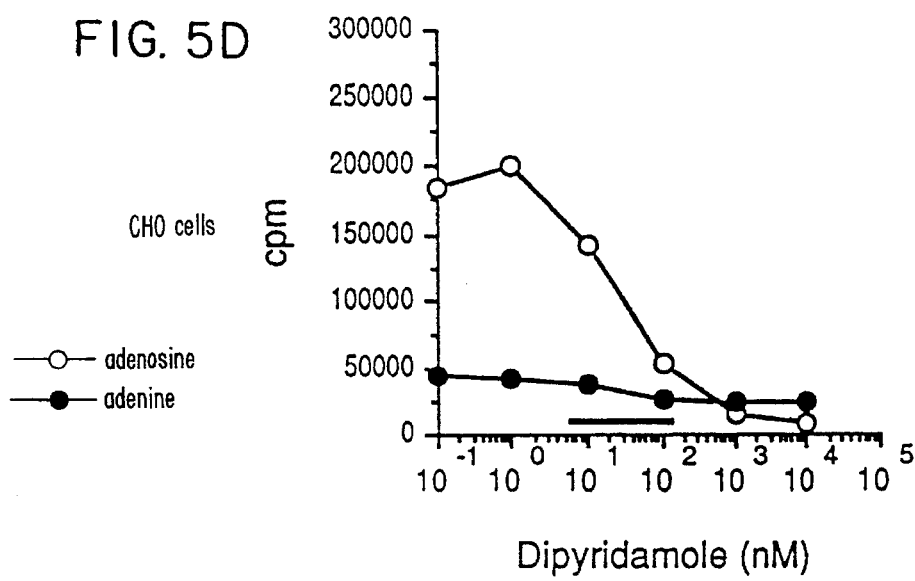

In contrast, as shown in FIGS. 5B and 5D, dipyridamole inhibited adenosine transport in a selective fashion with no effect on adenine transport in its therapeutic range (10–100 nM) (also shown as a bar in FIGS. 5B and 5D). Only high concentrations of dipyridamole (10–100 μM) inhibited adenine transport, as described by Scholtissek et al, *Biochem. Biophys. Acta*, 158:435–447 (1968); and Plagemann et al, *J. Membr. Biol.*, 81:255–262 (1984).

Transport of other nucleosides, including thymidine and uridine, was affected by vesnarinone in a manner similar to adenosine, while transport of uracil (a pyrimidine nucleobase) was inhibited like adenine, but to a lesser extent.

These data indicate that vesnarinone inhibits nucleoside and nucleobase transport, but via a different mechanism from that of dipyridamole. Furthermore, FIGS. 5A and 5C illustrate that the degree of inhibition of nucleoside transport by vesnarinone was similar to that of nucleoside incorporation demonstrated in FIG. 1A. These results indicate that most of the inhibition of [$^3$H]nucleoside incorporation by vesnarinone is due to inhibition of nucleoside transport by vesnarinone.

Nucleoside transport inhibitors, such as dipyridamole or NBMPR, are known to rescue cell proliferation from the cytotoxic effects of 5-fluorouridine (5-FUd) or high dose thymidine, by inhibiting transport of this cytotoxic nucleoside analog or thymidine (Aronow et al, *Mol. Cell Biol.*, 6:2957–2962 (1986)). Thus, vesnarinone was tested to determine whether it has a similar effect using CHO cells.

Figure 6A:
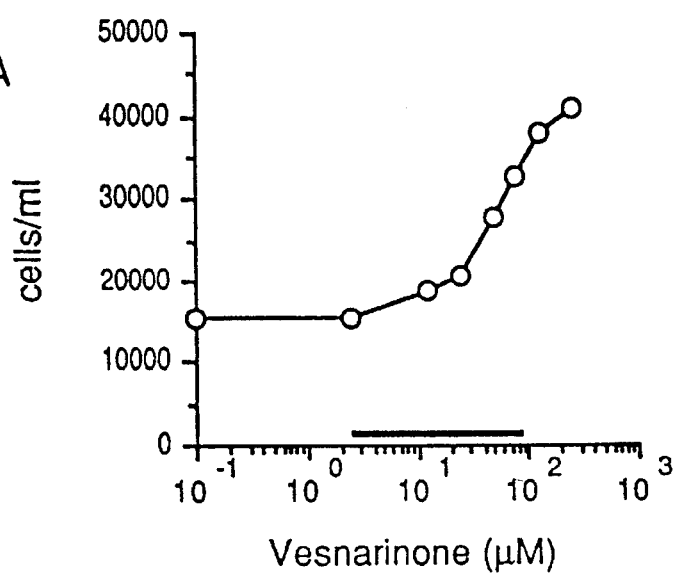
FIGS. 6A–6B show cell numbers counted 120 hrs after incubation of CHO cells with 50 nM 5-Fud in the presence of 0–250 µM vesnarinone (FIG. 6A); or 1–10 µM dipyridamole (FIG. 6B).

More specifically, $1 \times 10^4$ CHO cells/ml were incubated with 50 nM 5-FUd in the presence of 0–250 μM vesnarinone or 1.0–10 μM dipyridamole, and cell numbers were counted after 120 hrs of incubation. The results are shown in FIGS. 6A–6B.

Figure 6B:
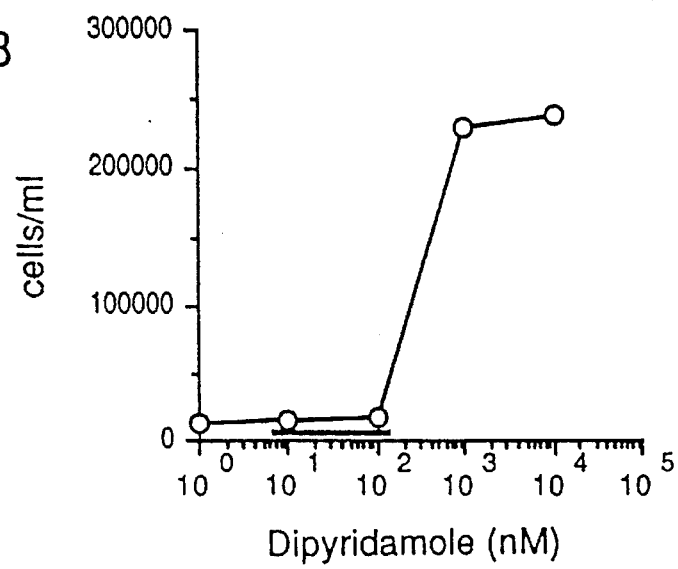

As shown in FIG. 6B, dipyridamole significantly reversed the cytostatic effects of 5-FUd. Also as shown in FIG. 6A, vesnarinone demonstrated a similar ability to rescue the cells in a dose-dependent manner. It was difficult to demonstrate a similar effect when higher ($\geq 100$ nM) or lower ($\leq 10$ nM) doses of 5-FUd were used, likely due to the anti-proliferative effects of vesnarinone itself. These data provide additional support that vesnarinone acts as an inhibitor of nucleoside transport.

In this Example it was demonstrated that vesnarinone inhibits nucleoside and nucleobase transport, while other high affinity inhibitors of nucleoside transport, such as dipyridamole, have a markedly reduced ability to inhibit nucleobase transport. Although much higher concentrations of vesnarinone are required, with vesnarinone, it is notable that the inhibitory effects on nucleoside and nucleobase transport in vitro were observed within the therapeutic range of vesnarinone in vivo (2–80 μM), implying that these effects in vitro may be related to some clinical effects of vesnarinone.

Inhibition of nucleoside and nucleobase uptake into cells by vesnarinone could result in the inhibition of cell proliferation, especially where nucleobase synthesis is more dependent on the salvage pathway. Cell types, such as polymorphonuclear leukocytes, certain brain cells, intestinal mucosal cells or erythrocytes have little or no de novo synthesis capability for nucleobases, whereas other cells such as hepatocytes have an active de novo synthesis system. Therefore, these in vitro observations may delineate the cause of agranulocytosis, a major side effect of vesnarinone observed in some patients (OPC-8212 Multicenter Research Group, *Cardiovasc. Drugs, Ther.*, 4:419–425 (1990); Feldman et al, *Am. J. Cardiol.*, 68:1203–1210 (1991); Feldman et al, *N. Engl. J. Med.*, 329:1419–155 (1993); and Packer, *N. Engl. J. Med.*, 329:201–202 (1993)).

The decrease in nucleoside and nucleobase transport by vesnarinone may also play a role in the inhibitory effect on HIV-1 replication (Meyerhans et al, *J. Virol.*, 68:535–540 (1994); O'Brien et al, *J. Virol.*, 68:1258–1263 (1994); and Gao et al, *Proc. Natl. Acad. Sci. USA*, 90:8925–8928 (1993)). Recently, triggering decreases or an imbalance in nucleobase pools has been reported to reduce the rate of reverse transcription of HIV-1 in cells or to induce aborted viral replication (Ullman et al, *Mol. Cell. Biol.*, 3:1187–1196 (1983)); Aronow et al, *J. Biol. Chem.*, 260:6226–6233 (1985); and Scholtissek et al, *Biochem. Biophys. Acta*, 158:435–447 (1968)).

Finally, inhibition of adenosine transport may provide the link with another novel aspect in the action of vesnarinone. Dipyridamole is proposed to cause a localized increase in adenosine concentration through its inhibition of adenosine transport into cells (Plagemann et al, *Biochem. Biophys. Acta*, 947:405–443 (1988)). Adenosine is known to induce an increase in cAMP (Fox et al, *Ann. Rev. Biochem.*, 47:655–686 (1978)), dilation of coronary arteries (Fox et al, *Ann. Rev. Biochem.*, 47:655–686 (1978)), an increase in cerebral blood flow (Heistad et al, *Am. J. Physiol.*, 240:775–780 (1981)), a decrease in TNF-α production (Parmely et al, *J. Immunol.*, 151:389–396 (1993)), and a decrease in platelet aggregation (Dawicki et al, *Biochem. Pharmacol.*, 34:3965–3972 (1985)), through its binding to specific adenosine receptors on cell surface membranes. Vesnarinone might similarly increase blood concentrations of adenosine by inhibiting adenosine transport, thus explaining some of the therapeutic benefit of vesnarinone in heart disease (Feldman et al, *N. Engl. Med.*, 329:149–155 (1993);

and Packer, *N. Engl. J. Med.*, 329:201–202 (1993)) or in the reduction of TFN-α production (Maruyama et al, *Biochem. Biophys. Res. Comm.*, 195:1264–1271 (1993); and Matsumori et al, *Circul.*, 89:955–958 (1994)).

EXAMPLE 2

A. Effect of Vesnarinone on Expression of ZEBRA and on Productive Replication of EBV The human Burkitt's lymphoma cell line, Akata, provided by Dr. Kenzo Takada (Takada, *Int. J. Cancer*, 33:27–32 (1984); and Takada et al, *Virus Genes*, 5:147–156 (1991)), was cultured at 37° C. in RPMI 1640 medium supplemented with 15% (v/v) heat-inactivated FCS, and 20 µg/ml gentamicin.

The cell progression of Akata cells was arrested by culturing of the cells for 96 hrs in the presence of 1.5% (v/v) DMSO (Sigma, St. Louis, Mo.) (Sawai et al, *Exp. Cell Res.*, 187:4–10 (1990); and Takase et al, *Cell Growth Differ.*, 3:515–521 (1992)). Then, the DMSO-arrested Akata cells were washed twice with PBS, and transferred, at a density of $10^6$/ml, to RPMI 1640 medium containing vesnarinone at different concentrations ranging from 0–100 µg/ml, prepared as described below.

10 mg vesnarinone was dissolved in 0.5 ml of 2.0N HCl and then diluted with 5.0 ml of $H_2O$ and 4.0 ml of RPMI 1640 medium. After neutralization with 2.0N NaOH (about 0.5 ml), the vesnarinone solution (1.0 mg/ml) was immediately filtered through a 0.45 µm Millipore filter, and diluted to the desired concentration in culture medium.

1 hr after transfer (release from DMSO), a goat $F(ab')_2$ fragment of anti-human IgG antibody (Organon Teknika, Durham, N.C.) was added at a concentration of 50 µg/ml to induce productive EBV replication (Takagi et al, *Virology*, 185:309–315 (1991)).

3 hrs and 20 hrs after treatment with the anti-IgG, the cells were harvested for flow cytometric detection of the BamHI Z replication activator (ZEBRA), and for in situ detection of EBV DNA, respectively.

For flow cytometric detection of ZEBRA, after a 60 min fixation with 70% (v/v) ethanol at 4° C., $10^6$ cells were centrifuged, and washed with PBS. After a 5 min incubation in 250 µl of PBS containing 0.5 %(v/v) Tween-20, 2.0% (w/v) BSA and 1.5% (w/v) human γ-globulin (Sigma) at room temperature, 10 µl of the hybridoma supernatant of mouse monoclonal anti-EB1/ZEBRA (Z-125, provided by Dr. Evelyn Manet) (Mikaelian et al, *J. Virol.*, 67:734–742 (1993)) was added, and the mixture was incubated at 4° C. for 120 min. The cells were then washed with PBS, and further treated with 5.0 µl of a FITC-conjugated $F(ab')_2$ fragment of affinity purified sheep anti-mouse IgG (F/P molar ratio=3.2, Sigma) at 4° C. for 60 min. The cells were washed with PBS again, and analyzed by flow cytometry (Epics Profile, Coulter), monitoring fluorescence (520–540 nm) in a logarithmic scale with 488 nm excitation. The positivity for ZEBRA was calculated by a non-linear least squares method (Takase et al, *J. Immunol. Methods*, 118:129–138 (1989)).

For detection of EBV DNA in cells, an in situ hybridization technique using the kit from ENZO Diagnostics (Syosset, N.Y.) was employed (Takagi et al, *Virol.*, 185:309–315 (1991)). The hybridization procedure was performed basically according to the instructions of the manufacturer.

More specifically, cells coated on a glass slide were fixed in acetone at room temperature for 10 min. Target and probe DNA (biotinylated probe of EBV BamHI Z fragment) were denatured at 94° C. for 4 min, and hybridized for 20 min at 37° C. For detection of the specifically hybridized DNA, the slide was treated with an avidin-biotinylated horseradish peroxidase complex, and developed by 3-amino-9-ethylcarbazole and hydrogen peroxide. Positivity for EBV DNA was determined by the presence of red-colored grains and at least 1000 cells were examined under light microscopy. Cells in which productive EBV replication is ongoing are plainly distinguished by the strong staining (Takagi et al, *Virol.*, 185:309–315 (1991)). It should be noted that both positivity for EBV DNA in in situ hybridization and multiple linear forms of EBV DNA demonstrated in Southern blotting (BamHI digestion and NJhet DNA probed) (Raab-Traub et al, *Cell*, 47:883–889 (1986)) are dramatically reduced by acyclovir pretreatment in anti-IgG treated Akata cells. The results are shown in FIG. 7.

Figure 7:
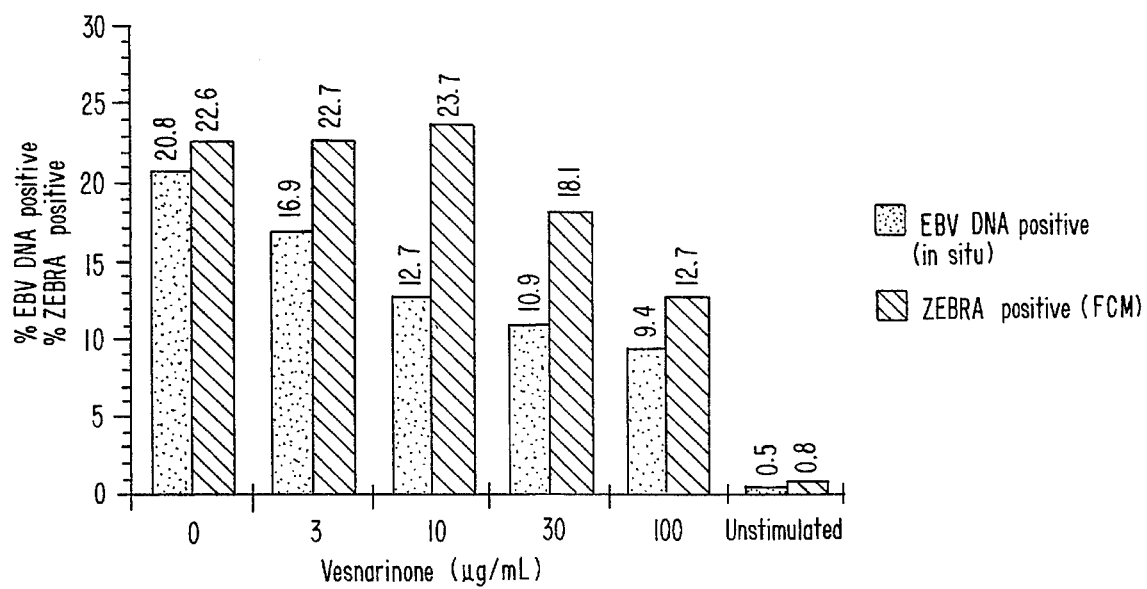
FIG. 7 shows the actual percentage of DMSO-released Akata cells stimulated with 50 µg/ml of anti-IgG antibody in the presence of vesnarinone at concentrations ranging from 0–100 µg/ml, and which express ZEBRA, as determined by flow cytometry (FCM), and the number of cells positive for EBV DNA, as determined by in situ hybridization.

As shown in FIG. 7, the population of EBV producing cells, as measured by EBV DNA, gradually decreased in the presence of vesnarinone in a dose-dependent manner. On the other hand, the degree of positivity for ZEBRA was not decreased by vesnarinone at concentrations less than or equal to 10 µg/ml. A shift in the curve was observed at concentrations greater than 30 µg/ml. Thus, susceptibilities to vesnarinone of expression of an early gene of the productive cycle, i.e., ZEBRA, and productive replication of EBV genome could be distinguished.

B. Effects of Vesnarinone on Expression of Early Antigens

DMSO-arrested Akata cells were washed, and transferred to culture medium containing 30 µg/ml vesnarinone. 1 hr after release and transfer, the above-described anti-IgG antibody was added at a concentration of 50 µg/ml. 3 hrs and 20 hrs after treatment with the anti-IgG, the cells were harvested for the detection of EBV early antigens ZEBRA (BZLF1 product) by Western immunoblot.

More specifically, cells were washed with PBS, and then lysed at 4° C. in a buffer comprising 25 mM Tris-HCl (pH 7.4), 50 mM NaCl, 0.5% (w/v) sodium deoxycholate, 2.0% (v/v) Nonidet P-40, 0.2% (w/v) SDS, 1.0 µmM phenylmethane sulfonyl fluoride (PMSF), 10 µg/ml aprotinin, 10 µM leupeptin, and 100 µM sodium orthovanadate. After centrifugation, lysates were prepared for electrophoresis as described by Laemmli, *Nature*, 227:680–685 (1970). An amount of lysate equivalent to $4.0 \times 10^5$ cells was used for each immunoblot analysis.

After electrophoretic transfer of proteins to nitrocellulose filters and blocking the filters with 20 mM Tris-HCl (pH 8.0), 125 mM NaCl, 0.1% (v/v) Tween-20, 2.0% (w/v) BSA, and 0.1% (w/v) sodium azide, the filters were incubated with the appropriate primary antibody. For detection of ZEBRA (EB1, BZLF1 gene product), the antibody used was mouse monoclonal anti-EB1 (Z-125); for the detection of R (BRLF1 product), the antibody used was the mouse monoclonal anti-R (R5A9, provided by Dr. Evelyn Manet); for the detection of EA-R (BHRF1 product), monoclonal anti-EA-R (5B11, provided by Dr. Elliott Kieff) (Pearson et al, *Virol.*, 160:151–161 (1987); and Henderson et al, *Proc. Natl. Acad. Sci. USA*, 90:8479–8483 (1993)), and for the detection of EA-D (BMRF1 product), the antibody used with the mouse monoclonal anti-EA-D (NEA-9240, DuPont, Boston, Mass. (Pearson et al, *Virol.*, 47:193–201 (1983); and Kiehl et al, *Virol.*, 184:330–340 (1991))).

Specific reactive bands were detected using anti-mouse secondary antibodies conjugated to alkaline phosphatase (Promega, Madison, Wis.) or horseradish peroxidase (Amersham) or ECL chemiluminescence (Amersham). That is, for detection of ZEBRA and R, alkaline phosphatase was used. For detection of EA-R and EA-D, horseradish peroxidase and the ECL chemiluminescence method was used (Amersham). Development was by the conventional methods, employing the colorogenic substrates bromochloroindolyl phosphate and nitroblue tetrazolium for alkaline phosphatase. The expression of ZEBRA reached a plateau level 3 hrs after stimulation and productive replication of EBV ceased 12 hrs after stimulation in this system. The results are shown in FIGS. 8A-SD.

Figure 8A:
Figure 8C:
Figure 8D:
Figure 9A:
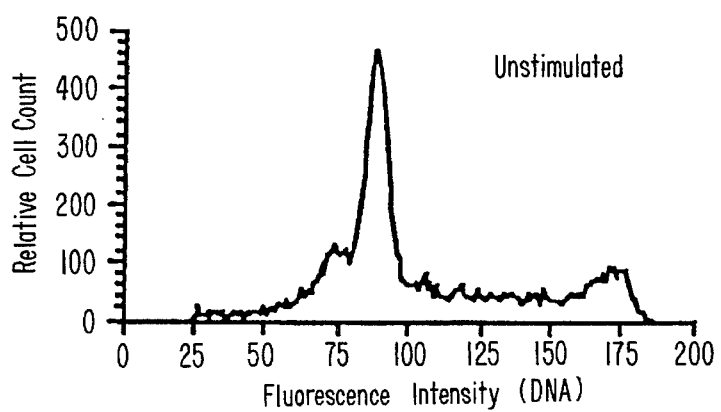
FIGS. 9A–9F represent flow cytometry analysis of DMSO-released Akata cells stimulated with 50 µg/ml of anti-IgG for 20 hrs in the presence of vesnarinone at concentrations ranging from 0–100 µg/ml. The control shows the results of samples without anti-IgG stimulation. The 2C peak corresponding to the DNA content of the G1 population appears around channel numbers 75 to 100.
Figure 9B:
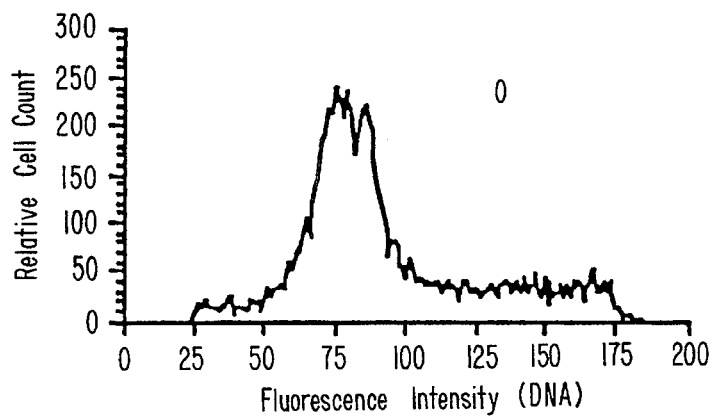
Figure 9C:
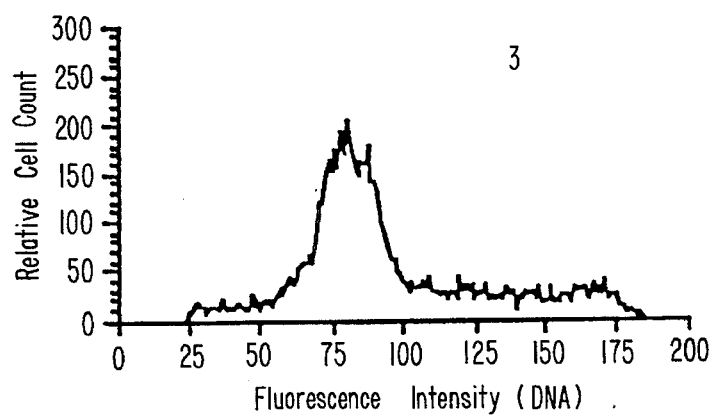
Figure 9D:
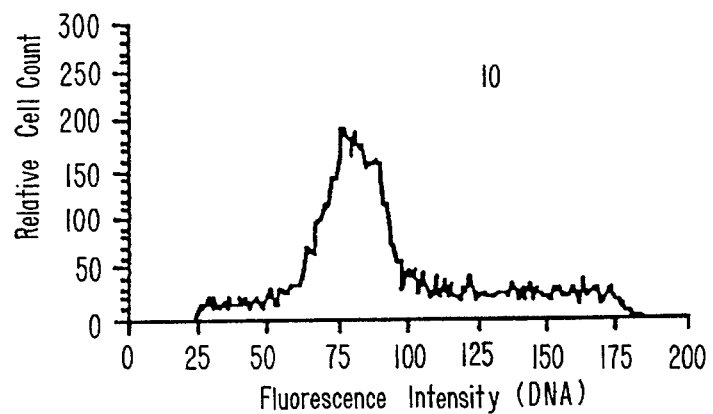
Figure 9E:
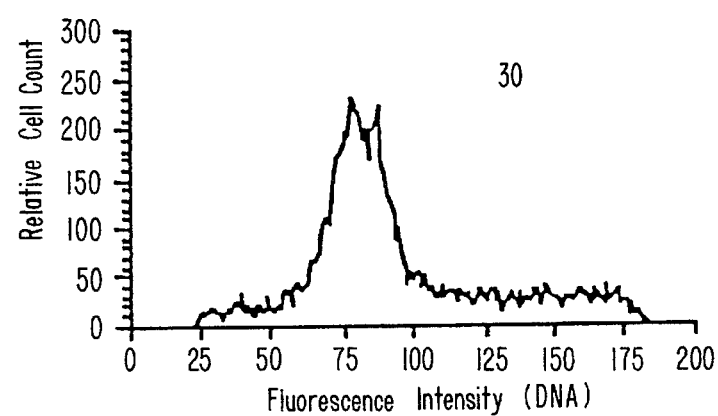
Figure 9F:
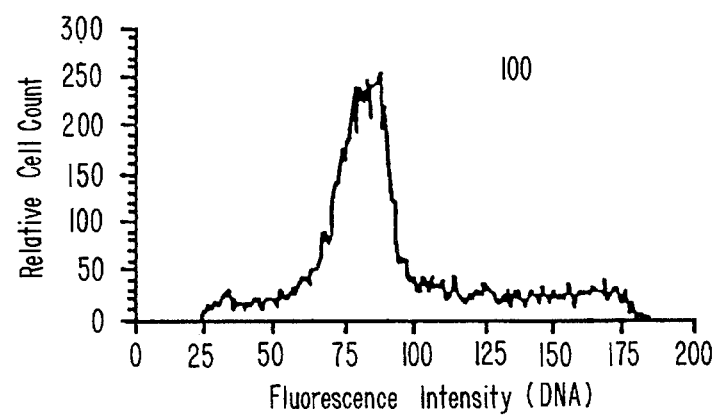
Figure 10A:
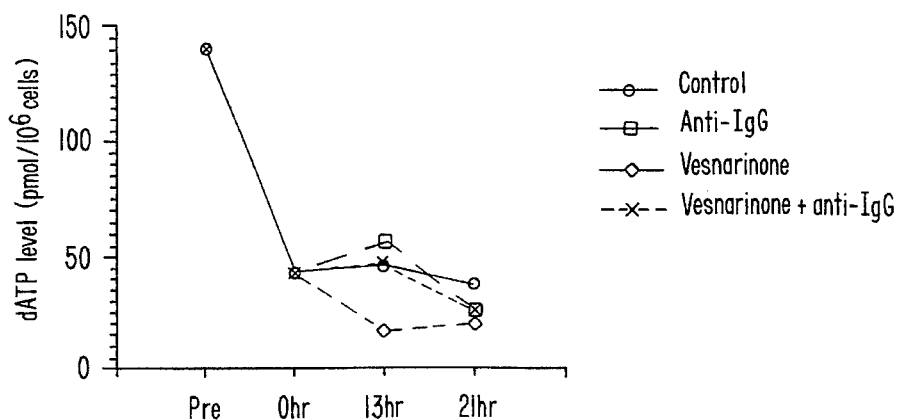
FIGS. 10A–10D show pmoles of dNTP extracted with 60% (v/v) ethanol from $10^6$ logarithmically growing DMSO-arrested Akata cells, Akata cells assayed 13 hrs and 21 hrs after DMSO-release without vesnarinone without anti-IgG stimulation (o), or with IgG stimulation (□), and Akata cells assayed 13 hrs and 21 hrs after DMSO-release with 100 µg/ml vesnarinone without (◊) anti-IgG stimulation or with anti-IgG stimulation (×), and quantitated by an enzymatic method.
Figure 10B:
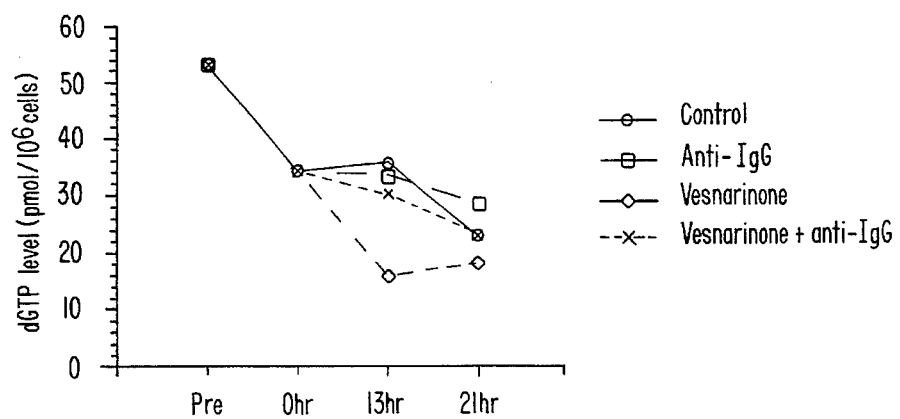
Figure 10C:
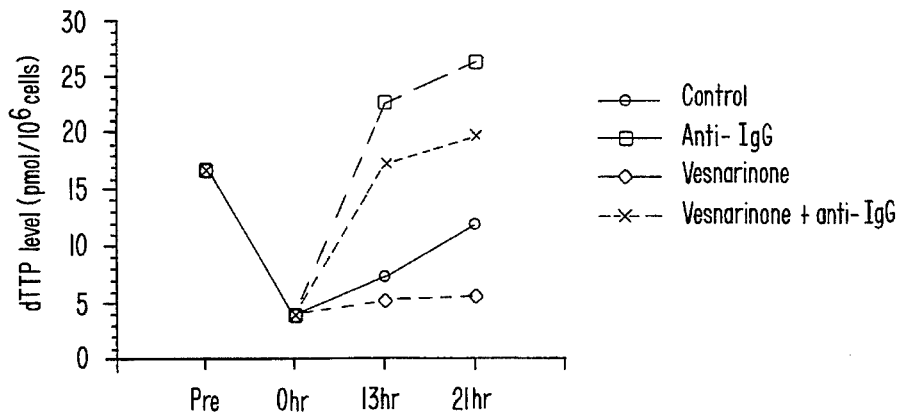
Figure 10D:
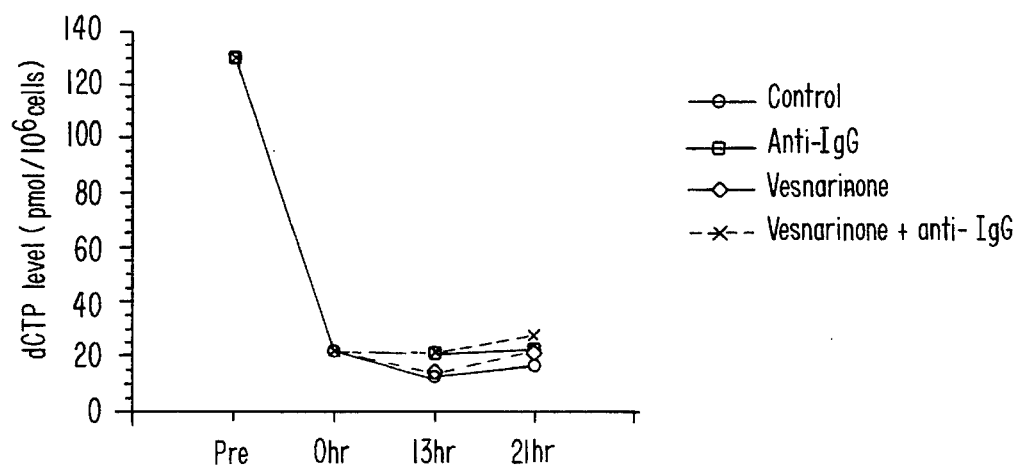

As shown in FIG. 8A, the expression of ZEBRA was suppressed 3 hrs after stimulation with anti-IgG to a limited extent in the presence of vesnarinone, comparable to the data presented in FIG. 7. As shown in FIG. 8B, another immediate early gene product, R was expressed virtually at the same level in the presence or absence of vesnarinone, 3 hrs and 20 hrs after stimulation. As shown in FIG. 8C, the bcl-2 homologous early gene product, EA-R was also expressed to the same degree 3 hrs and 20 hrs after stimulation. In contrast, as shown in FIG. 8D, expression of an EBV DNA polymerase cofactor, EA-D, which is expressed at a later time point than the other three early genes, was dramatically suppressed in the presence of vesnarinone, 20 hrs after stimulation.

C. Cellular DNA Content of Anti-IgG Treated DMSO-Released Akata Cells in the Presence of Vesnarinone During the productive phase of EBV replication, a broadening of the 2C peak of DNA has been noted. This phenomenon presumably contributed to the denaturation or disruption of chromosomal DNA as a part of the lytic process. In some cases, the extent of the change in the 2C peak correlated with the rate of EBV production. Thus, the 2C peak in anti-IgG treated DMSO-released Akata cells in the presence of vesnarinone was evaluated.

More specifically, DMSO-released Akata cells stimulated with 50 µg/ml of anti-IgG for 20 hrs in the presence of vesnarinone at concentrations ranging from 0–100 µg/ml as described above, were fixed overnight with 70% (v/v) ethanol at 4° C., and $10^6$ cells were centrifuged, and washed with PBS. Next, the fixed cells were incubated with 0.5 ml of 0.25 mg/ml ribonuclease (Sigma) in PBS at 37° C. for 20 min. Then, the cell suspension was mixed with 0.5 ml of propidium iodide (Calbiodiem, La Jolla, Calif.) solution (50 µg/ml in PBS), and after 60 min analyzed by flow cytometry (EPICS Profile, Coulter, Hialeah, Fla.), monitoring fluorescence (>600 nm) in a linear scale with 488 nm excitation (Takase et al, *Cell Growth Differ.*, 3:515–521 (1992)). The standard deviation of the G1 of peak of the DNA histogram was calculated by a non-linear least squares method (Takase et al, *J. Immunol. Methods.*, 118.:129–138 (1989)). The results are shown in FIGS. 9A–9F.

As shown in FIGS. 9A–9F, the distinctly broadened 2C peak, compared to the sharp 2C peak observed in control samples without anti-IgG treatment, were observed in samples treated with anti-IgG in the presence or absence of vesnarinone. These observations indicate that this characteristic of the lytic process observed in anti-IgG treated Akata cells was not prevented by vesnarinone, despite the reduction in EBV DNA replication.

D. dNTP Pools in Cells Treated with Vesnarinone

The profiles of four dNTPs in Akata cells were measured under several conditions, in logarithmically growing cells, in DMSO-arrested cells, in cells 13 hrs and 21 hrs after release from DMSO in the absence of vesnarinone, and in cells 13 hrs and 21 hrs after release from DMSO in the presence of 100 µg/ml vesnarinone.

More specifically, $10^7$ cells were washed with PBS, and vigorously suspended in 300 µl of cold 60% (v/v) ethanol (Tyrsted, *Exp. Cell Res.*, 91:429–440 (1975)). After a 10 min incubation on ice, the supernatant containing dNTPs was removed, frozen and evaporated with a rotary evaporator. The residue was dissolved in 100 µl of $H_2O$, and a 10 µl aliquot of this solution was used for the measurement of dNTP pool.

In order to quantitate the amount of each dNTP, an enzymatic method using DNA polymerase I and calf thymus DNA as a substrate was employed (Williams et al, *J. Biochem. Biophys. Methods*, 1:153–162 (1979)).

More specifically, 10 µl of the sample or a dNTP standard solution was mixed with 40 µl of the reaction buffer comprising 62.5 mM Tris-HCl (pH 7.8), 0.625 mM DTT, 0.125 mg/ml calf thymus DNA (Sigma), 0.625 mg/ml BSA, 10 mM $MgCl_2$, 6.25 µM three dNTPs, and 5.0 µCi/ml [$^3$H] dATP (ICN, Costa Mesa, CA), for measurement of dTTP, dCTP, and dGTP, or [$^3$H]dTTP (ICN), for measurement of dATP. The reaction solution was then mixed with 1.0 unit of *E. coli* DNA polymerase I (Boehringer Mannheim), and incubated for 40 min at 37° C. After completion of the reaction, the mixture was applied to Whatman DE-81 paper filters and radioactivity was determined using a liquid scintillation counter after three washes with 0.35 M $Na_2HPO_4$ (pH 7.5). Amounts of dNTP in the samples were calculated according to the calibration curves estimated by a set of standard dNTP samples. Vesnarinone at concentrations up to 100 µg/ml has no effect on the measurement of dNTP contents in this in vitro DNA polymerase assay. The results are shown in FIGS. 10A–10D.

As shown in FIGS. 10A–10D, the cellular content of all dNTPs were uniformly reduced following treatment with DMSO. Both dATP and dGTP displayed progressive reductions 13 hrs after release in the presence of vesnarinone without anti-IgG stimulation, despite the fact that the cellular contents were fairly well sustained at a relatively higher level or increased in the absence of vesnarinone. The cellular content of dTTP was demonstrated to be the smallest storage pool among the four dNTPs throughout all of the conditions. The reduced level of dTTP in DMSO-arrested cells was nearly restored to those in growing cells by 21 hrs after release. On the other hand, in cells released from DMSO in the presence of vesnarinone, the levels of dTTP remained quite low. The levels of dCTP remained low in the presence or absence of vesnarinone in cells after release.

In parallel, to measurement of the content of dNTPs in the untreated Akata cells after release, the dNTP pool in anti-IgG treated Akata cells was also measured in the same manner. The results are shown in FIGS. 10A–10D.

As shown in FIGS. 10A–10D, the level of dTTP at 12 hrs after treatment with anti-IgG (equivalently 13 hrs after release) was markedly elevated. This level of dTTP remained high 20 hrs after treatment, and was partially suppressed in the presence of vesnarinone. As for the three other dNTPs, such an increase in content as observed in dTTP was not demonstrated. The effects of vesnarinone on dNTP in anti-IgG stimulated cells was smaller than that in unstimulated cells except for dTTP.

E. Effects of Vesnarinone on Productive Replication of EBV in Growing Cells

Akata cells were maintained in growth phase for 7 days in culture medium with or without 20 µg/ml vesnarinone (pre-treatment). The cells were spun down, and then transferred to fresh culture medium with or without 20 µg/ml vesnarinone (post-treatment). 1 hr later, anti-IgG was added to the cultures at a final concentration of 50 µg/ml, and the cells were harvested for in situ hybridization of EBV DNA 24 hrs later as described above. The results are shown in FIG. 11.

Figure 11:
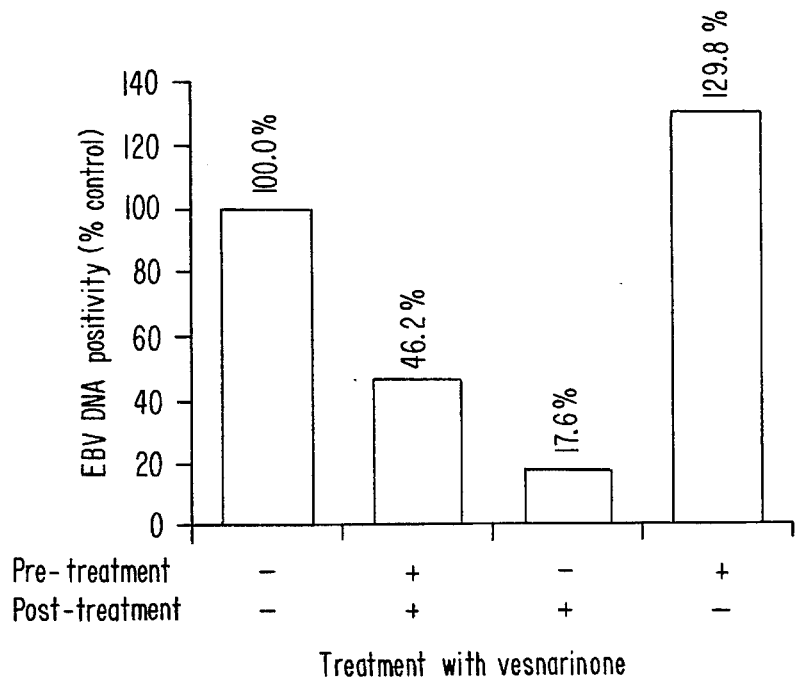
FIG. 11 shows the frequency of logarithmically growing Akata cells demonstrating productive replication of EBV when cultured in medium containing 20 µg/ml vesnarinone for 7 days (pre-treatment), 24 hrs after stimulation with 50 µg/ml anti-IgG in the presence of (+) or absence (−) of 20 µg/ml vesnarinone, determined using in situ hybridization. Also shown, are cells subsequently resuspended in fresh medium with (post-treatment +) or without (post-treatment −) 20 µg/ml vesnarinone, and then stimulated with 50 µg/ml of anti-IgG. The results are presented as percentages relative to the value in vesnarinone-untreated cells.

As shown in FIG. 11, treatment of the cells with vesnarinone for a longer period prior to (pre-treatment+post-treatment) or just prior to (solely post-treatment) addition of anti-IgG antibody reduced the level of positivity for EBV DNA compared to untreated cells. Cells treated with vesnarinone only concurrently with anti-IgG treatment displayed a more profound reduction of EBV production. In addition, in the face of pre-treatment alone, the degree of positivity for EBV DNA was higher. Thus, cell synchronously entering the lytic cycle may be more susceptible to vesnarinone.

Effects of Vesnarinone on Expression of Molecules Related to Latent Phase of EBV Infection The effects of vesnarinone on the expression of molecules related to the latent phase of EBV infection using four different EBV containing human B cell lines, were examined, i.e., cells carrying two different subgroups of EBV, type A and type B (Adldinger et al, *Virol.*, 141:221–234 (1985); Zimber et al, *Virol.*, 196:900–904 (1993); and Gregory et al, *Nature*, 349:612–614 (1991)). The cell lines included Akata (type A, group I), Raji (type A, group III), P3HR1 (type B, group I) (ATCC No. HTB-62), and Jijoye (type B, group III) (ATCC No. CCL-87). The molecules examined were a latent nuclear protein, EBNA2, a latent membrane protein, LMP1, and an anti-apoptotic host component, bcl-2. Generally, group I cell lines exhibit negligible amounts of EBNA2, LMP1, and bcl-2, in contrast to group III lines that possess distinctively large amounts of these molecules. These differences between the two phenotypes have been related to the sensitivity to induce apoptosis, and the ability to induce the productive phase of EBV infection (Henderson et al, *Cell*, 65:1107–1115 (1991); and Gregory et al, *Nature*, 349:612–614 (1991)).

More specifically, the cells cultured in medium with or without 20 µg/ml vesnarinone for 7 days were harvested for Western blotting as described above. For detection of EBNA2, LMP1, and bcl-2, the mouse monoclonal anti-EBNA2 (PE2, Accurate, Westbury, NY) (Young et al, *N. Engl. J. Med.*, 321:1080–1085 (1989)), the mouse monoclonal anti-LMP1 (S12, provided by Dr. David A. Thorley-Lawson) (Mann et al, *J. Virol.*, 55:710–720 (1985)), and the monoclonal anti-bcl-2 (bcl-2/124, Accurate) (Pezzella et al, *Am. J. Pathol.*, 137:225–232 (1990)), respectively, were used. The ECL chemiluminescence method was used for the detection of these proteins. Under these conditions, cell growth in the presence of vesnarinone was reduced to 80–90% of the control cultures when cell numbers were assessed. The results are shown in FIGS. 12A–12C.

Figure 12A:
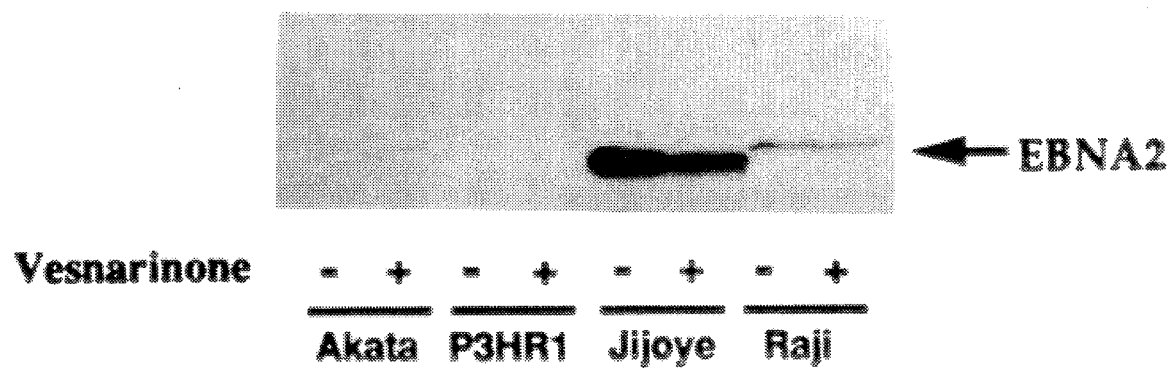
Figure 12B:
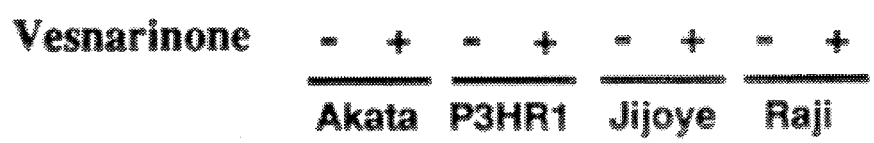
Figure 12C:

As shown in FIGS. 12A–12C, vesnarinone did not induce these molecules in the group I lines, nor did the vesnarinone alter levels of expression of these molecules in the group III lines. Thus, EBV–containing cells expressing different gene products, or susceptibility to apoptosis may be differentially sensitive to vesnarinone.

G. Effects of Vesnarinone on Thymidine Kinase Activity in Anti-IgG Treated Akata Cells It has been known that thymidine kinase plays an important role in metabolic synthesis of dTTP (Sasayama et al, *Heart Vessels*, 2:23–28 (1986); and Feldman et al, *Am. Heart J.*, 116:771–777 (1988)), and an EBV early gene, BXLF1, encodes a thymidine kinase which is distinguishable from the cellular counterpart by a broad range of nucleoside or nucleobase analogues as substrates, and a relatively stronger resistance to dTTP.

Thus, thymidine kinase activity was measured in Akata cells treated with 50 µg/ml of anti-IgG which were cultured in the presence of vesnarinone at a concentration of 100 µg/ml, and harvested 12 hrs later, according to the method of Turenne-Tessier et al, *J. Virol.*, 57:1105–1112 (1986) with several modifications.

More specifically, cells were washed with PBS, and immediately frozen with dry ice/ethanol. The pellet of frozen cells was suspended in 100 µl of kinase extraction buffer comprising 50 mM Tris (pH 8.0), 50 mM KCl, 1.0 mM $MgCl_2$, 1.0 mM ATP, 1.0 mM DTT, 5.0% (v/v) glycerol, 80 µg/ml aprotinin, 40 µM leupeptin and 1.0 mM PMSF, and incubated on ice for 30 min after a brief sonication. The nuclei were removed by high speed centrifugation for 15 min and the supernatant (kinase extract) was aliquoted and stored at –70° C. The protein concentration of the kinase extract (about 4.0 mg/ml) was determined using standard Bradford Reagent (Bio-Rad Protein Assay Kit, Bio-Rad Laboratories, Hercules, Calif), with BSA as a protein standard.

5.0 µl of the kinase extract was incubated at 37° C. with 35 µl of kinase reaction buffer comprising 150 mM phosphate (pH 7.5), 20 mM ATP, 20 mM $MgCl_2$, 40 mM KCl, 1.0 mM DTT, 10 mM NaF and 20 µM [$^3$H]thymidine (6.7 Ci/mmole, ICN) for 5 or 15 min. The reaction was terminated by placing on ice, and an addition of 4.0 µl of 0.5 M EDTA (pH 8.0). For measurement of dTTP-resistant thymidine kinase activity, a kinase reaction buffer additionally containing 100 µM dTTP (Pharmacia) was used.

The amount of phosphorylated [$^3$H]thymidine derivatives formed during the reaction was determined by applying the reaction mixtures onto Whatman DE-81 paper filters, which were then washed four times in 1.0 mM ammonium formate (pH 8.0), and once in ethanol before drying and liquid scintillation counting. An addition of vesnarinone into this in vitro assay system at concentrations up to 100 µg/ml, did not display any inhibition of the thymidine kinase activity. The results are shown in FIG. 13A.

As shown in FIG. 13A, a high activity of whole thymidine kinase in growing cells was profoundly reduced in DMSO-arrested cells, and restored to a small extent 13 hrs after release. A further additional increase in thymidine kinase activity was observed in cells treated with anti-IgG, and this increase was partially inhibited in the presence of vesnarinone.

Next, thymidine kinase assays were performed in the same manner in the presence of 100 µM dTTP, which preferentially suppresses the thymidine kinase of cellular origin. The results are shown in FIG. 13B.

As shown in FIG. 13B, there were high levels of dTTP-resistant thymidine kinase in anti-IgG treated cells. These observations indicate that the increase in thymidine kinase activity observed in anti-IgG treated cells is likely due to an expression of the EBV thymidine kinase gene (BXLF1). In addition, the increase in dTTP-resistant thymidine kinase was also partially suppressed by vesnarinone treatment.

As shown in this Example, vesnarinone inhibits the productive phase of EBV infection in a cell system that offers a number of distinct advantages. That is, following anti-IgG antibody treatment of Akata cells, there is a rapid induction of the productive viral cycle. Moreover, introduction of arrest of cell cycle progression followed by release, the treatment with anti-IgG antibody induces a more efficient and synchronous replication of EBV within 12 hrs, before the cells enter S-phase. This rapid and synchronous entry into the productive phase enables one to elucidate events in a clearer fashion. Also, the events can be analyzed independently of those associated with host cell proliferation.

In this system, vesnarinone markedly inhibited the productive replication of EBV genome in a dose-dependent manner. In contrast, little or no change was observed in the expression of the early genes associated with exit from the latent stage, including ZEBRA, R and EA-R. Further, the broadened 2C peak of DNA detected by flow cytometry in cells treated with anti-IgG antibody persisted in the presence of vesnarinone. This configuration of DNA is evidence for entry into the lytic cycle. These data, which characterize stimulated entry into the lytic phase, appeared independently of the effect of vesnarinone on productive replication of EBV genome detected by in situ hybridization. Only EA-D expression was markedly reduced by vesnarinone 20 hrs after anti-IgG stimulation. EA-D is a co-factor of the EBV DNA polymerase, and is generally expressed at a later time point than the other three early genes. One possible explanation for this dissociation of effects on early gene expression is that EA-D may be EBV replication unit related to the EBV replication unit (Kiehl et al, Virol., 184:330–340 (1991); and Daibata et al, Virol., 196:900–904 (1993)), and its expression may be regulated in part by the status of EBV DNA replication itself.

In the DMSO-released Akata cells, dTTP represented the smallest deoxynucleobase pool, and was one of the major targets of vesnarinone treatment. In addition, levels of dATP and dGTP were also influenced to the same degree by vesnarinone treatment. There have been several lines of evidence linking depletion or alteration of deoxynucleobase pools with reduction of DNA viral replication (Datta et al, Proc. Natl. Acad. Sci. USA, 77:5163–5166 (1980)), and an increase in the rate of mutation of reverse transcription of retroviruses (Vartanian et al, Proc. Natl Acad. Sci. USA, 91:3092–3096 (1994))

Anti-viral agents such as acyclovir, act as a competitor to dGTP in EBV DNA replication after modification to the active acyclovir triphosphate (Datta et al, Proc. Natl. Acad. Sci. USA, 77:5163–5166 (1980)). The alterations in dTTP, dATP, and dGTP pool size by vesnarinone may reasonably explain the suppression of EBV replication observed in this system. Among four dNTPs, dTTP was the only dNTP induced particularly by the anti-IgG treatment, and this increase in dTTP level in the cells seemed to be attributed to the expression of the EBV thymidine kinase which is recognized as an early gene product. The substantial suppression of the increase in dTTP level in anti-IgG treated cells by treatment with 100 μg/ml vesnarinone was comparable to the suppression of induction of thymidine kinase activity observed under the same culture conditions. The expression of this early gene (BXLF1) may be affected by the treatment of this drug at this concentration similarly to the case of ZEBRA.

These studies indicate that vesnarinone should prove to have therapeutic benefit in disorders where reactivation of EBV is observed, and where productive replication of EBV plays an important role.

While the invention has been described in detail, and with reference to specific embodiments thereof, it will be apparent to one of ordinary skill in the art that various changes and modifications can be made therein without departing from the spirit and scope thereof.

What is claimed:

1. A method for inhibiting nucleoside and nucleobase transport in mammalian cells, comprising exposing said mammalian cells to a pharmaceutically effective amount of a carbostyril derivative represented by the following general formula (1), or a pharmaceutically acceptable salt thereof:

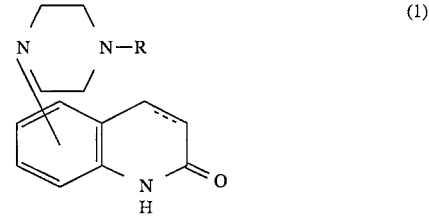

wherein R is a benzoyl group which may optionally have lower alkoxy groups on the phenyl ring as substituents and the carbon-carbon bond in the 3 and 4 positions of the carbostyril skeleton is a single bond or double bond.

2. The method of claim 1, wherein said carbostyril is 3,4-dihydro-6-[4-(3,4 -dimethoxybenzoyl)-1-piperazinyl]-2(1H)-quinoline or a pharmaceutically acceptable salt thereof.

* * * * *